US012692290B2

(12) United States Patent
Mrsny et al.

(10) Patent No.: US 12,692,290 B2
(45) Date of Patent: Jul. 28, 2026

(54) MODULATORS OF TIGHT JUNCTION PERMEABILITY

(71) Applicant: The University of Bath, Bath (GB)

(72) Inventors: Randy Mrsny, Bath and North East (GB); Alistair Taverner, Bath and North East (GB); Khaled Almansour, Bath and North East (GB)

(73) Assignee: The University of Bath (GB)

( * ) Notice: Subject to any disclaimer, the term of this patent is extended or adjusted under 35 U.S.C. 154(b) by 873 days.

(21) Appl. No.: 18/001,321

(22) PCT Filed: Jun. 11, 2021

(86) PCT No.: PCT/EP2021/065842
§ 371 (c)(1),
(2) Date: Dec. 9, 2022

(87) PCT Pub. No.: WO2021/250260
PCT Pub. Date: Dec. 16, 2021

(65) Prior Publication Data
US 2023/0234987 A1 Jul. 27, 2023

(30) Foreign Application Priority Data
Jun. 12, 2020 (GB) .................................... 2009007

(51) Int. Cl.
*C07K 7/08* (2006.01)
*A61P 43/00* (2006.01)
(52) U.S. Cl.
CPC ................ *C07K 7/08* (2013.01); *A61P 43/00* (2018.01)
(58) Field of Classification Search
None
See application file for complete search history.

(56) References Cited

U.S. PATENT DOCUMENTS

| | | |
|---|---|---|
| 2008/0318837 A1 | 12/2008 | Quay |
| 2010/0273212 A1 | 10/2010 | Reed |

FOREIGN PATENT DOCUMENTS

| | | |
|---|---|---|
| AU | 2005203401 | 2/2006 |
| CN | 101233151 | 7/2008 |
| CN | 101687911 | 3/2010 |
| CN | 106661086 | 5/2017 |
| JP | 2004517865 | 6/2004 |
| JP | 2017528417 | 9/2017 |
| WO | 2008137681 A2 | 11/2008 |

OTHER PUBLICATIONS

Anderson, James M., and Christina M. Van Itallie. "Physiology and function of the tight junction." Cold Spring Harbor perspectives in biology 1.2 (2009): a002584.

Cunningham, Kevin E., and Jerrold R. Turner. "Myosin light chain kinase: pulling the strings of epithelial tight junction function." Annals of the New York Academy of Sciences 1258.1 (2012): 34-42.

Eto, Masumi. "Regulation of cellular protein phosphatase-1 (PP1) by phosphorylation of the CPI-17 family, C-kinase-activated PP1 inhibitors." Journal of Biological Chemistry 284.51 (2009): 35273-35277.

Fasano, Alessio, et al. "The enterotoxic effect of zonula occludens toxin on rabbit small intestine involves the paracellular pathway." Gastroenterology 112.3 (1997): 839-846.

Freedman, John C., Archana Shrestha, and Bruce A. McClane. "Clostridium perfringens enterotoxin: action, genetics, and translational applications." Toxins 8.3 (2016): 73.

Kondoh, M., and K. Yagi. "Tight junction modulators: promising candidates for drug delivery." Current medicinal chemistry 14.23 (2007): 2482-2488.

Krug, Susanne M., et al. "Angubindin-1, a novel paracellular absorption enhancer acting at the tricellular tight junction." Journal of Controlled Release 260 (2017): 1-11.

Krug, Susanne M., et al. "Sodium caprate as an enhancer of macromolecule permeation across tricellular tight junctions of intestinal cells." Biomaterials 34.1 (2013): 275-282.

Lemmer, Hendrik JR, and Josias H. Hamman. "Paracellular drug absorption enhancement through tight junction modulation." Expert opinion on drug delivery 10.1 (2013): 103-114.

McCartney, Fiona, John P. Gleeson, and David J. Brayden. "Safety concerns over the use of intestinal permeation enhancers: A mini-review." Tissue barriers 4.2 (2016): e1176822.

Pinheiro, Anderson S., et al. "Structural signature of the MYPT1-PP1 interaction." Journal of the American Chemical Society 133.1 (2011): 73-80.

Shen, Le, et al. "Myosin light chain phosphorylation regulates barrier function by remodeling tight junction structure." Journal of cell science 119.10 (2006): 2095-2106.

Tanaka, Junko, et al. "Interaction of myosin phosphatase target subunit 1 with the catalytic subunit of type 1 protein phosphatase." Biochemistry 37.47 (1998): 16697-16703.

Terrak, Mohammed, et al. "Structural basis of protein phosphatase 1 regulation." Nature 429.6993 (2004): 780-784.

Toth, Attila, et al. "Study of the subunit interactions in myosin phosphatase by surface plasmon resonance." European journal of biochemistry 267.6 (2000): 1687-1697.

Turner, Jerrold R., et al. "Physiological regulation of epithelial tight junctions is associated with myosin light-chain phosphorylation." American Journal of Physiology-Cell Physiology 273.4 (1997): C1378-C1385.

Wong, Vivian, and Barry M. Gumbiner. "A synthetic peptide corresponding to the extracellular domain of occludin perturbs the tight junction permeability barrier." The Journal of cell biology 136.2 (1997): 399-409.

(Continued)

*Primary Examiner* — Sergio Coffa
(74) *Attorney, Agent, or Firm* — FisherBroyles, LLP; Adam K. Whiting; Adelaide K. Leitzel

(57) ABSTRACT

The invention relates to compounds capable of modulating the permeability of junctions between epithelial cells, and their use to facilitate delivery of substances such as therapeutic and diagnostic agents across epithelial surfaces. In particular the invention relates to the identification of key amino acids in the known permeation enhancer PIP250 and the provision of new permeation enhancing peptides with more transient activity, thus providing faster epithelial recovery.

19 Claims, 9 Drawing Sheets

(56)        References Cited

OTHER PUBLICATIONS

Zihni, Ceniz, et al. "Tight junctions: from simple barriers to multifunctional molecular gates."cell biology 17.9 (2016): 564-580.
Almansour et al., "Mechanistic studies of a cell-permeant peptide designed to enhance myosin light chain phosphorylation in polarized intestinal epithelia", Journal of Controlled Release, 279, 208-219, 2018.
Maher et al., "Intestinal permeation enhancers for oral peptide delivery", Advanced Drug Delivery Reviews, 106, 277-319, 2016.
Taverner et al., "Enhanced paracellular transport of insulin can be achieved via transient induction of myosin light chain phosphorylation", Journal of Controlled Release, 210, 189-197, 2015.
Uniparc:UPI000923B1E7, 3 pages.

A)

B)

A)

B)

A)

B)

A

B

*Figure 5 (contd.)*
C
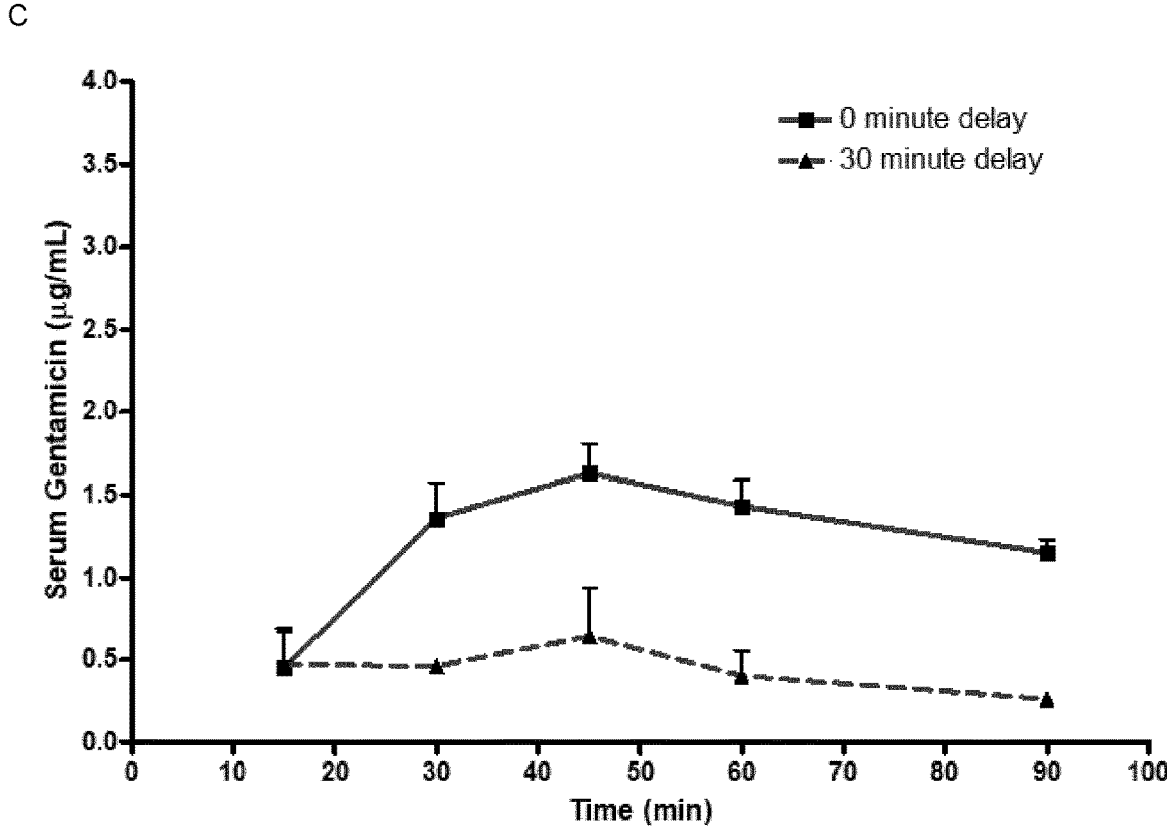
D
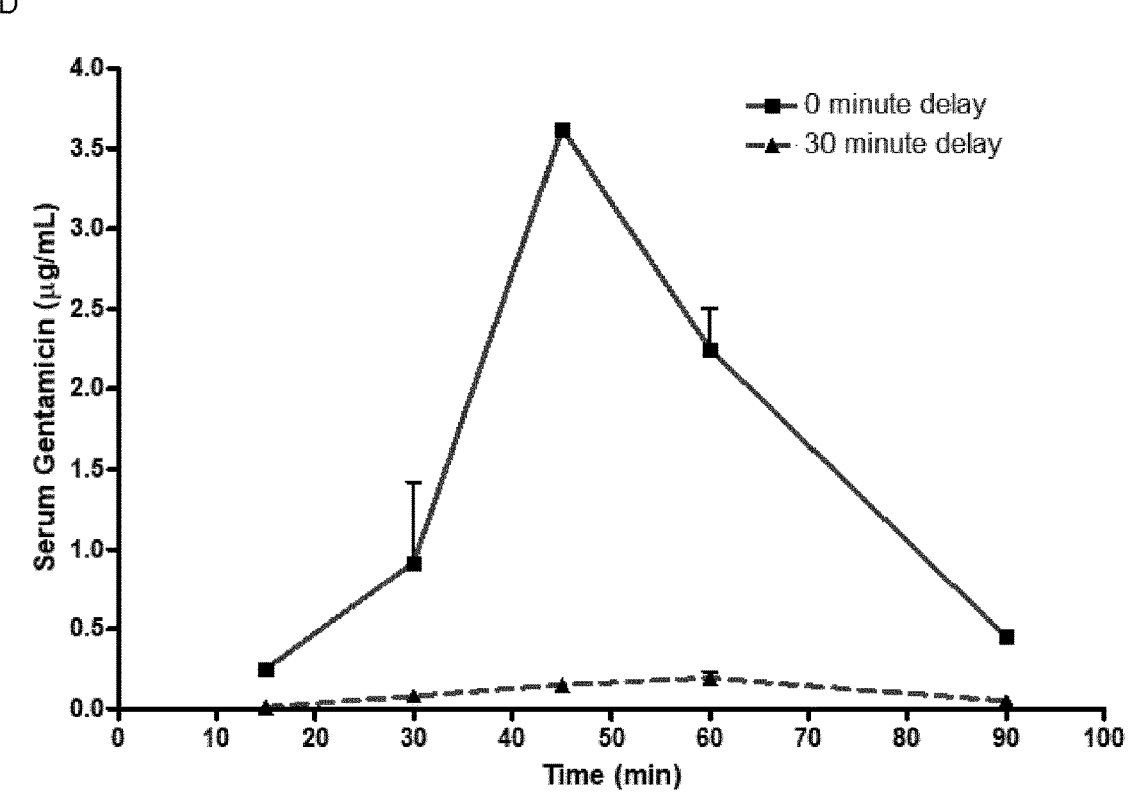

MODULATORS OF TIGHT JUNCTION PERMEABILITY

CROSS-REFERENCE

This application is a 371 National Stage filing and claims the benefit under 35 U.S.C. § 120 to International Application No. PCT/EP2021/065842, filed 11 Jun. 2021, which claims priority to Great Britain Application No. GB2009007.2, filed 12 Jun. 2020, each of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, is named 4553.017US1_Sequence_Listing.txt and is 4 kilobytes in size.

Field of the Invention

The present invention relates to compounds capable of modulating the permeability of junctions between epithelial cells, and their use to facilitate delivery of substances such as therapeutic and diagnostic agents across epithelial surfaces.

Background

The intestinal epithelium is a semi-permeable barrier that limits the absorption of large, hydrophilic molecules of molecular weight of >~500 Da. Thus, crossing this barrier is a significant obstacle to many drugs in several classes if given orally, including of therapeutic peptides and water-soluble antibiotics. The intestinal epithelium is composed of a single layer of cells that resist movement of large, hydrophilic molecules from the gut lumen that limit drug movement through cells, referred to as the transcellular route. This leaves the possibility for large hydrophilic molecules to enter the body from the gut lumen by moving between adjacent epithelial cells that is referred to as the paracellular space. A critical element to impeding movement of solutes through the paracellular route is a multi-protein complex organized at the apical neck of intestinal epithelial cells that hold them in very close proximity to one another; this complex is known as the tight junction (TJ) [1]. The TJ protein complex is composed of intracellular proteins, such as the zonula occludens family (e.g. ZO-1, ZO-2, ZO-3) that anchor the complex to the cytoskeleton via an actin/myosin ring, transmembrane proteins that include occludin, tricellulin, and claudins that are organized to establish the physical extracellular barrier that impedes paracellular solute movement, and a wide array of intracellular regulatory proteins that control the dynamic properties of the paracellular barrier through modifications of both intracellular and transmembrane protein TJ components [2].

A wide variety of TJ modulators have been investigated as a method of altering the barrier function of epithelia to improve the uptake of poorly absorbed drug molecules through the paracellular route [3]. Various components of the TJ have been targeted. Synthetic peptides have been shown to increase TJ permeability by emulating extracellular domains of occludin [4] or specific claudin proteins. Analogues of bacterial toxins such as Zonula Occludens Toxin, *Clostridium perfringens* enterotoxin, and *C. perfringens* iota-toxin have been shown to enhance permeability by disruption of ZO-1 [5], claudin-4 [6], and tricellulin [7], respectively. Sodium caprate has been shown to enhance permeability by decreasing tricellulin at TJs [8]. Many more permeation enhancers have been promising in in vitro testing and some have been tested clinically [9] [10], but in vivo applications of these approaches have typically been limited by low bioavailability or safety concerns [11]. As an alternative to physically disrupting or disorganizing protein-protein interactions occurring between extracellular domains of TJ proteins, efforts have been made to alter TJ permeability properties by affecting the regulatory proteins that dynamically control TJ function. STUDIES WITH non-specific phosphatase inhibitors, ETC.(REFS).

One of the major dynamic regulatory controls of TJ permeability involves the phosphorylation of myosin light chain (MLC) at Ser-19. Phosphorylated MLC (pMLC) results in a contraction of the TJ-associated actin/myosin cytoskeleton; this contraction leads to an increase in the TJ permeability properties [12] [13]. TJ permeability will return to its normal state once pMLC returns to its non-phosphorylated state, defining the dynamic nature of this mechanism. MLC phosphorylation is controlled by the enzymes myosin light chain kinase (MLCK) and myosin light chain phosphatase (MLCP) [14], with MLCP dominating in the normal state of low TJ permeability. Under conditions of chronic inflammation MLCK will dominate, resulting in the increase in TJ permeability associated with such a pathology. In a more dynamic situation, and which appears to occur in response to eating, transient increased levels of pMLC increase TJ permeability to provide a secondary mechanism to absorb essential nutrients. It is this dynamic process of transiently enhancing TJ permeability induced by nutrients that provides a provocative opportunity to increase the absorption of drugs that are poorly absorbed following oral administration.

MLCP is a holoenzyme consisting of a catalytic protein phosphatase subunit (PP1), a myosin targeting subunit (MYPT1), and a 38 kDa subunit of unknown function [15]. Additionally, the inhibitory subunit CPI-17 binds to MLCP when phosphorylated at Thr-38 (pCPI-17) and inhibits the enzyme's action [16]. MYPT1 binding to PP1 causes a dramatic increase in the affinity of MLC as a substrate for the enzyme, making it a highly specific phosphatase [17]. Without MYPT1 bound, PP1 has greatly reduced de-phosphorylation activity on MLC, therefore this protein/protein interaction is vital for the effective action of MLCP. A number of amino acid residues and sequences that are key to this interaction have been identified on MYPT1 and PP1. The sequence of Met-1 to Phe-38 on MYPT1 had been shown to increase the specificity of PP1 for MLC, however to a lesser degree than full length MYPT1 [18]. A shorter sequence from Asp-23 to Phe-38 is able to bind to PP1 but does not increase the specificity [19]. This suggests that residues within the sequence of amino acids 23-38 are required for binding and the N-terminus plays a role in the targeting of PP1 to MLC. Specifically, it appears that the binding motif [35]KVKF[38] is key to the binding between PP1 and MYPT1 but is insufficient to increase specificity for MLC. Val-36 and Phe-38 appear to bind to a specific hydrophobic pocket on PP1 [15].

We have previously studied two rationally designed permeable inhibitor of phosphatase (PIP) peptides based on sequences involved in MLCP interactions. PIP640 is based on a segment of pCPI-17 and PIP250 is based on the binding motif on MYPT1. Both peptides enhanced permeability by increasing pMLC levels [20].

SUMMARY OF THE INVENTION

The present invention relates to further peptides capable of increasing epithelial permeability, and having benefits compared to the peptide PIP250 described previously [20].

The invention provides an agent capable of increasing epithelial permeability, wherein the agent comprises a peptide of no more than 50 amino acids in length, said peptide comprising a core sequence of Formula I:

x3-k-x5-k          (Formula I)

wherein
x3 is selected from D-Phe, D-Ala, D-Leu and Gly;
x5 is selected from D-Val, D-Ala, D-Leu and Gly; and
x3 and x5 are not both D-Phe;
or a retro-inverso form of the core sequence of Formula I.

In some embodiments the peptide has a core sequence of Formula II:

x3-k-x5-ktk          (Formula II)

wherein
x3 is selected from D-Phe, D-Ala, D-Leu and Gly;
x5 is selected from D-Val, D-Ala, D-Leu and Gly; and
x3 and x5 are not both D-Phe;
or a retro-inverso form of the core sequence of Formula II.

The agent may be capable of crossing the plasma membrane of an epithelial cell. For example, it may be chemically modified, e.g. with a lipophilic moiety such as a lipid, (e.g. cholesterol), or any other moiety capable of increasing transit across the plasma membrane, such as cationic polymers and dendrimers.

Alternatively the peptide itself may be capable of crossing the plasma membrane without further chemical modification. Thus the peptide may comprise one or more additional sequence(s) capable of mediating transit across the plasma membrane. Such sequences may be designated "CPP" (cell penetrating peptide) sequences. Thus the peptide may comprise one or more CPP sequences.

The peptides PIP251 and PIP252 described herein possess additional sequences N- and C-terminal of their respective core sequence. These additional sequences comprise multiple positively charged residues and are believed, inter alia, to mediate transit across the plasma membrane.

Thus the peptide may comprise one of more positively charged residues (e.g. Lys or Arg, in the relevant D or L configuration) N-terminal and/or C-terminal of the core sequence.

For example, it may comprise the residues rr N-terminal of the core sequence, and/or krk C-terminal of the core sequence.

Thus, the peptide may comprise or may consist of the sequence:
rr-x3-k-x5-ktkkrk
a retro-inverso form thereof;
or a functional fragment or variant of either.

A functional fragment may be truncated from the N-terminal and/or C-terminal end. It will be understood that the core sequence of Formula I or Formula II (or the retro-inverso form thereof) will be maintained.

A functional variant may differ from one of the recited sequences (or the retro-inverso form thereof) by one or more amino acid substitutions, deletions or insertions. It may differ from the recited sequence at no more than 5 positions, e.g. no more than 4 positions, no more than 3 position, no more than 2 positions, or no more than 1 position. It will be understood that the core sequence of Formula I or Formula II (or the retro-inverso form thereof) may not vary.

The functional fragment or variant will retain the activity of increasing epithelial permeability. It may also retain the ability to cross the plasma membrane, although this may not be necessary if the peptide comprises a suitable chemical modification which facilitates membrane transit.

In some embodiments, x3 is D-Phe and x5 is selected from D-Val, D-Ala, D-Leu and Gly. In some embodiments, x5 is D-Ala and x3 is selected from D-Val, D-Ala, D-Leu and Gly.

In some embodiments, the core sequence of Formula I is akvk, fkak or akak, preferably akvk or fkak.

In some embodiments, the core sequence of Formula II is akvktk, fkaktk or akaktk, preferably akvktk or fkaktk.

Thus the peptide may comprise or consist of the sequence:
rrakvktkkrk
or
rrfkaktkkrk
a retro-inverso form of either;
or a functional fragment or variant thereof.

The peptide is no more than 50 amino acid residues in length, e.g. no more than 40 amino acid residues, no more than 30 amino acid residues, no more than 20 amino acid residues, no more than 15 amino acid residues, e.g. 11, 12, 13 or 14 amino acid residues in length.

The peptide is at least 5 residues in length, e.g. at least 6, at least 7, at least 8, at least 9, at least 10 or at least 11 residues in length, e.g. at least 10 or at least 11 residues in length.

In some embodiments the peptide is between 10 and 20 residues in length, e.g. between 10 and 15 residues in length.

The peptide may have the formula $R^1$—Z—$R^2$ wherein:
$R^1$ is H, $C_{1-4}$ alkyl, acetyl, formyl, benzoyl or trifluoro-acetyl;
$R^2$ is OH or $NH_2$;
and Z represents a peptide sequence as described herein.
Particular preferred agents of the invention are:
H-rrakvktkkrk-$NH_2$
and
H-rrfka ktkkrk-$NH_2$ The agent of the invention, and specifically the peptide component of that agent, is capable of increasing epithelial permeability. In particular, it is capable of increasing the permeability of tight junctions between epithelial cells, especially the epithelia of the gastrointestinal tract or respiratory tract.

Without wishing to be bound by theory, the peptide component, and more particularly the core sequence of Formula I, is believed to be capable of inhibiting the interaction between PP1 and MYPT1, e.g. by binding to PP1.

When the agent is administered to an epithelium in conjunction with a particular substance, it is capable of increasing passage of that substance across the relevant epithelium.

The agents of the invention exhibit certain desirable properties as compared to known permeation enhancers such as PIP250. For example, epithelia may show faster recovery to baseline permeability when treated with the agents of the invention than when treated with PIP250. Thus the agents of the invention may exhibit a better balance between therapeutic or diagnostic effects and toxicity, since the epithelial tight junctions remain open for a shorter time period, allowing transit of desired substances, but reducing the time for unwanted materials such as toxins or pathogens to cross the epithelium.

The invention further provides an agent as described herein for use in therapy.

The invention further provides a pharmaceutical composition comprising an agent as described herein and a pharmaceutically acceptable carrier. The composition may be formulated to permit or facilitate transit of the agent across the plasma membrane of a target epithelial cell. For example, it may be a liposome formulation.

The composition may further comprise a substance to be delivered across an epithelial surface.

The invention further provides a kit comprising:
(i) a first composition comprising an agent as described herein; and
(ii) a second composition comprising a substance to be delivered across an epithelial surface.

The first and second compositions may, optionally, be pharmaceutical formulations, and each may independently comprise a pharmaceutically acceptable carrier.

The invention further provides the use of an agent as described herein for the manufacture of a medicament.

The invention further provides an agent or a pharmaceutical composition as described herein for use in increasing permeability of an epithelial surface.

The invention further provides a method of increasing permeability of an epithelial surface comprising administering an effective amount of an agent or a pharmaceutical composition as described herein to the epithelium.

The invention further provides an agent or a pharmaceutical composition as described herein for use in a method of delivering a substance across an epithelial surface. The method may comprise administering said substance in conjunction with the agent or pharmaceutical composition.

The invention further provides a method of delivering a substance across an epithelial surface comprising administering said substance in conjunction with an agent or a pharmaceutical composition as described herein.

The method may be carried out in vitro, ex vivo or in vivo.

The substance may be a diagnostic or therapeutic agent, or any other substance which it is desirable to introduce across an epithelial surface.

The substance may be peptidic. The term "peptidic" as used herein includes compounds that are composed of or comprise a linear chain of amino acids linked by peptide bonds and include peptides, polypeptides and proteins. The term "peptide" is used for molecules that consist of between 2 and 50 contiguous amino acids, while "polypeptide" is used for molecules that are made up of more than 50 contiguous amino acids. The term protein may be used interchangeably with polypeptide but may also encompass complexes of one or more peptides or polypeptides associated by covalent or non-covalent bonds.

The substance may be a nucleic acid, such as a DNA or RNA. For example, it may be an aptamer or a gene therapy agent.

Alternatively the substance may be any other suitable molecule, including non-peptidic organic molecules. The substance may be a small molecule, i.e. having a molecular weight of 500 Da or less, or a macromolecule (over 500 Da).

The agents of the invention may find particular use oral delivery of proteinaceous therapeutic agents which would otherwise be subjected to proteolysis in the gastrointestinal tract, e.g. in the intestine or stomach.

The invention includes the combination of the aspects and preferred features described except where such a combination is clearly impermissible or expressly avoided.

SUMMARY OF THE FIGURES

Embodiments and experiments illustrating the principles of the invention will now be discussed with reference to the accompanying figures in which.

DETAILED DESCRIPTION OF THE INVENTION

Figure 1:
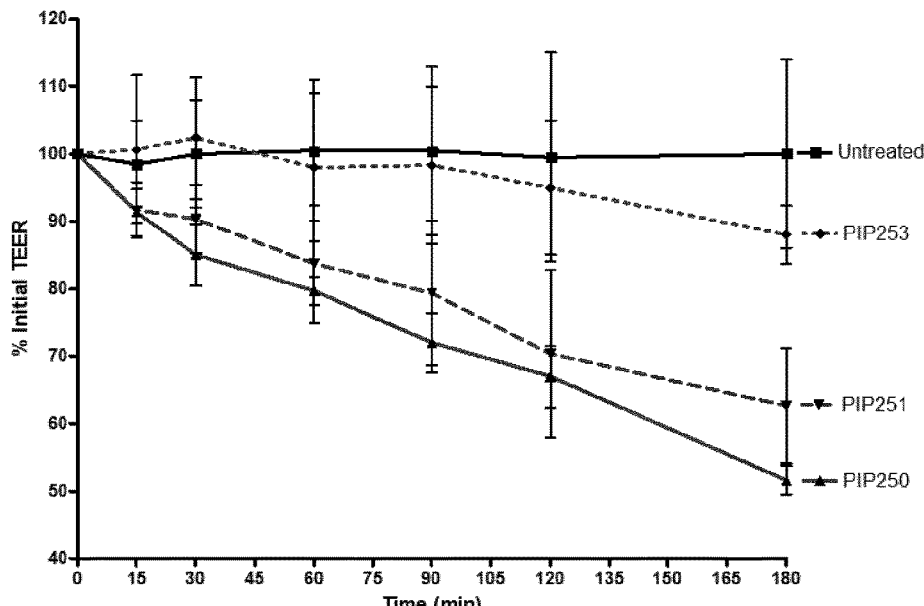
FIG. 1. Effect of 5 mM PIP250-254 series on the TEER of Caco-2 monolayer in vitro. A) Effect of changing Phe-P3 (PIP250) to either an alanine (PIP251) or aspartic acid (PIP253). B) Effect of changing Val-P5 (PIP250) to either alanine (PIP252) or aspartic acid (PIP254). One-way ANOVA showed significant difference between data sets in both A) and B) ($p < 0.05$). PIP250, PIP251 and PIP252 data sets were significantly different from control in bonferroni post-test ($p < 0.05$). PIP253 and PIP254 not significant.
Figure 1:
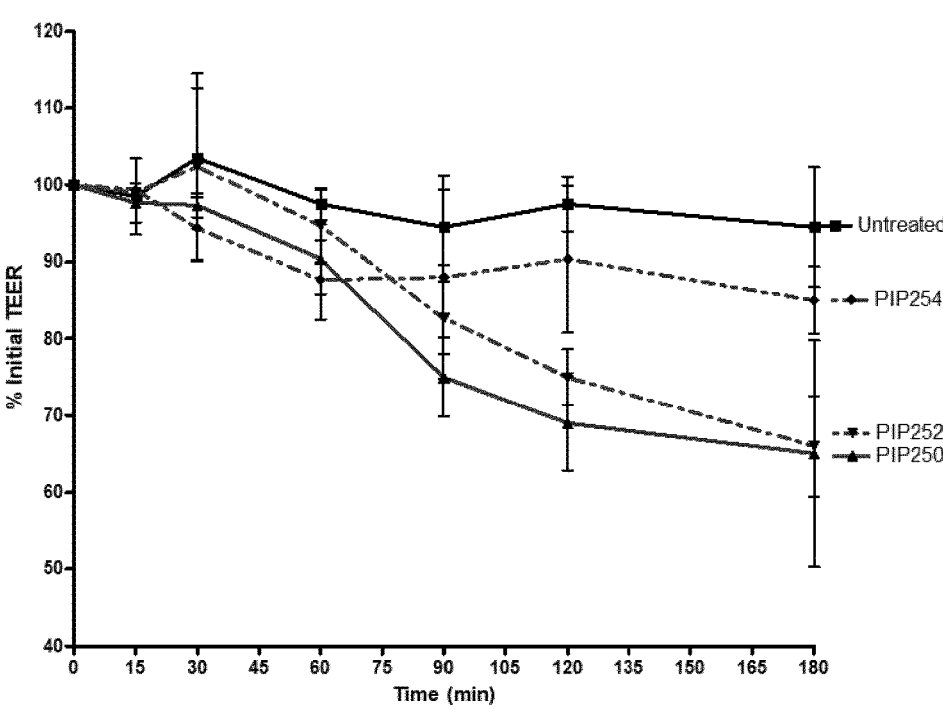

Aspects and embodiments of the present invention will now be discussed with reference to the accompanying figures. Further aspects and embodiments will be apparent to those skilled in the art. All documents mentioned in this text are incorporated herein by reference.

The present invention is based on the development of strategies to open the paracellular route between adjacent cells in an epithelium by controlling the dynamic opening and closing of tight junctions by harnessing an endogenous control mechanism. The strategies related to the provision of peptide compounds designed to target specific cellular targets and to have specific action on those targets.

Throughout the present description and claims the conventional three-letter and one-letter codes for naturally occurring amino acids are used, i.e.

A (Ala), G (Gly), L (Leu), I (Ile), V (Val), F (Phe), W (Trp), S (Ser), T (Thr), Y (Tyr), N (Asn), Q (Gln), D (Asp), E (Glu), K (Lys), R (Arg), H (His), M (Met), C (Cys) and P (Pro)

By "naturally occurring" in this context is meant the 20 amino acids encoded by the standard genetic code, sometimes referred to as proteinogenic amino acids.

When using the single letter code, lower case letters are used for amino acid residues of the D-configuration, and upper case letters for amino acid residues of the L-configuration. For non-chiral amino acid residues (e.g. glycine), either may be used. When the three letter code is used, the configuration D- or L- is typically indicated explicitly. If no configuration is shown, the D-configuration should be assumed.

When applied to a given amino acid sequence, the term "retro-inverso" is used to indicate an alternative form containing the same residues, in the opposite configuration (L or D), and in which the order of the residues from N- to C-terminus is reversed. The term is often used to refer to a reversed-sequence all-D version of a conventional peptide consisting of L-form residues. In this specification, however, the peptides are typically all-D, especially for peptides intended for use in the gastrointestinal tract, since all-D peptides are considerably more resistant to proteolysis than all-L peptides. Thus the term "retro-inverso" is used to denote a reversed-sequence all-L version of a given sequence. All-L peptides may be more suitable for use in the context of the respiratory tract and other epithelia.

The terminal groups present at the N- and C-termini of the peptide backbone may be designated $R^1$ and $R^2$ respectively. Thus $R^1$ is bonded to the nitrogen atom of the N-terminal amino group and $R^2$ is bonded to the C-terminal carbonyl carbon atom.

$R^1$ is hydrogen ("H" or "Hy"), $C_{1-4}$ alkyl, acetyl, formyl, benzoyl or trifluoroacetyl.

Thus, for example, $R^1$=hydrogen ("H-" or "Hy-") indicates a free primary amino group at the N-terminus. (The other hydrogen atom of the N-terminal amino group is generally invariant, regardless of the nature of $R^1$.)

$R^2$ is typically "—OH" or "—NH$_2$", which indicate a C-terminal carboxyl (COOH) or amido (CONH$_2$) group respectively.

In some embodiments of the invention, $R^1$ is H (or Hy) and $R^2$ is NH$_2$.

Epithelia

The agents and compositions described herein can be used to increase permeability of an epithelium, i.e. one or more layers of epithelial cells, which may be referred to as an "epithelial surface".

This surface may be in vitro, ex vivo, or in vivo surface.

Non-limiting examples include epithelia of the gastrointestinal tract (e.g. the epithelium of the mouth, eosohagus, stomach, small intestine, large intestine, rectum or anus), the respiratory tract (e.g. epithelium of the nasal cavity, pharynx, larynx, trachea, bronchioles or lung), or any other suitable epithelium including but not limited to those of the cornea, cervix or vagina.

Immortalized cell lines of epithelial cells, for example of the epithelial cell types described immediately above are especially contemplated.

Subjects

The agents, compositions and methods of the invention may be applied to subjects of any species which have an epithelium with tight junctions. Mammalian subjects are particularly preferred. The subject may be of any mammalian species, including rodents (e.g. mice, rats), lagomorphs (e.g. rabbits), felines (e.g. cats), canines (e.g. dogs), equines (e.g. horses), bovines (e.g. cows), caprines (e.g. goats), ovines (e.g. sheep), other domestic, livestock or laboratory animals, or primates (e.g. Old World monkey, New World monkey, apes or humans).

Substances for Delivery

The agent of the invention is typically administered in conjunction with a substance for delivery across an epithelium. The agent and the substance for delivery may be provided in the same composition (e.g. in admixture) or in separate compositions.

In some embodiments, it will typically be desirable that they are provided in the same composition. However, depending on the specific components, this may not be possible, for example if they have incompatible requirements for formulation. Thus, in other embodiments, it may be desirable that they are provided in separate compositions.

When formulated in separate compositions, they will typically be administered at substantially the same site. They may be administered by the same or different routes. Typically, they will be administered within one hour of one another, e.g. within 30 minutes, within 15 minutes, within 5 minutes or within 1 minute of one another, e.g. substantially simultaneously. When they are not administered simultaneously, it may be advantageous to deliver he agent of the invention first, so that it has time to exert its effect on permeability of the relevant epithelium before introduction of the substance to be delivered across the epithelium.

The agents of the invention may be used to deliver a wide range of substances across epithelia, including small molecules, peptidic substances (peptides, polypeptides and proteins), nucleic acids and other organic macromolecules.

The substance for delivery may be a therapeutic or diagnostic agent.

Peptidic therapeutic agents may include hormones and other agonists of hormone receptors, such as insulin and analogues thereof, GLP-1 and other GLP-1 receptor agonists such as exendin-4 and analogues thereof, parathyroid hormone, growth hormone, somatostatin and analogues thereof such as octreotide, calcitonin and erythropoietin. They may include cytokines (e.g. GM-CSF and interleukins), chemokines, interferons, antibiotics and antibodies.

Specific examples of therapeutic peptides include the following, any of which may be employed in the context of the compositions and methods of the invention:

| Generic name | Trade name ® | Classification/Application |
| --- | --- | --- |
| Eptifibatide | Integrilin | Anti-platelet drug |
| Octreotide | Sandostatin | Somatostatin analogue |
| Desmopressin | DDAVP | Synthetic vasopressin analogue |
| Vasopressin | Pitressin | Antidiuretic peptide |
| Lanreotide | Somatuline LA | Somatostatin analogue |
| GnRH | HRF | Peptide hormone |
| Cyclosporin | Neoral | Immunosuppressant peptide |
| Leuprorelin/ Leuprolide acetate | Prostap | GnRH agonist |
| Terlipressin | Glypressin | Synthetic vasopressin analogue |
| Mifamurtide | Mepact | Osteosarcoma |
| Buserelin | Suprefact | GnRH agonist |
| Goserelin | Zoladex | GnRH super agonist |
| Icatibant | Firazyr | Hereditary angioedema |

-continued

| Generic name | Trade name ® | Classification/Application |
|---|---|---|
| Triptorelin | Decapeptyl SR | GnRH agonist |
| Nafarelin | Synarel | GnRH agonist |
| Histrelin | Vantas | GnRH agonist |
| Abarelix | Plenaxis | Prostate cancer |
| Cetrorelix | Cetrotide | GnRH antagonist |
| Vancomycin | Vancocin matrigel | Antibiotic peptide |
| Linaclotide | Linzess | IBS |
| Degarelix | Firmagon | GnRH antagonist |
| Bivalirudin | Angiox | Anticoagulant |
| Tetracoactide | Synacthen | ACTH analogue |
| Tetracosactide | Synacthen | Corticotrophin analogue |
| Salmon calcitonin | Miacalcic | Anti-osteoporotic peptide |
| Nesiritide | Natrecor | human B-type natriuretic peptide |
| Glucagon | Glucagen | Antidiabetic peptide |
| Liraglutide | Victoza | GLP-1 analogue agonist peptide |
| Teduglutide | Gattex/Nycomed | GLP-2 analogue agonist peptide |
| Pramlintide | Symlin | Analogue of Amylin |
| teriparatide | Forsteo | rh parathyroid hormone (analogue) |
| Exenatide | Byetta | Exendin-4 |
| Enfuvirtide | Fuzeon | Antiviral peptide |
| rh Insulin | Actrapid | Antidiabetic peptide |
| rh Insulin | Insuman rapid | Antidiabetic peptide |
| rh Insulin | Humulin S | Antidiabetic peptide |
| Insulin lispro | Humalog | Analogue of rh insulin |
| Insulin glulisine | Apidra | Analogue of rh insulin |
| Insulin aspart | NovoRapid | Analogue of rh insulin |
| Insulin detemir | Levemir | Analogue of rh insulin |
| Insulin glargine | Lantus | Analogue of rh insulin |
| Glatiramer acetate | Copaxone | Immunomodulator peptide |
| Ecallantide | Kalbitor | Hereditary angioedema |
| Mecasermin | Increlax | rh insulin like growth factor-I |
| rh PTH | Preotact | Anti-osteoporotic peptide |

["rh" = recombinant human]

Nucleic acid therapeutic agents may include any appropriate nucleic acid, whether DNA or RNA. They may include gene therapy agents such as plasmid or viral vectors, and aptamers.

Other organic molecules may include lipids, carbohydrates including oligosaccharides and polysaccharides, and drug molecules of any type including antibiotics such as aminoglycoside antibiotics (e.g. gentamicin).

The substance may be an antibody. The term "antibody" is used to include a functional fragment or derivative of an antibody, or a synthetic antibody or synthetic antibody fragment. an antibody may be employed for therapeutic or diagnostic purposes.

In view of today's techniques in relation to monoclonal antibody technology, antibodies can be prepared to most antigens. The antigen-binding portion may be a part of an antibody (for example a Fab fragment) or a synthetic antibody fragment (for example a single chain Fv fragment [scFv]). Suitable monoclonal antibodies to selected antigens may be prepared by known techniques, for example those disclosed in "Monoclonal Antibodies: A manual of techniques", H Zola (CRC Press, 1988) and in "Monoclonal Hybridoma Antibodies: Techniques and Applications", J G R Hurrell (CRC Press, 1982). Chimaeric antibodies are discussed by Neuberger et al (1988, 8th International RICMP7164916 Biotechnology Symposium Part 2, 792-799).

Monoclonal antibodies (mAbs) are particularly useful and are a homogenous population of antibodies specifically targeting a single epitope on an antigen.

Antigen binding fragments of antibodies, such as Fab and Fab2 fragments may also be used/provided as can genetically engineered antibodies and antibody fragments. The variable heavy (VH) and variable light (VL) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) Proc. Natl. Acad. Sd. USA 81, 6851-6855).

That antigenic specificity is conferred by variable domains and is independent of the constant domains is known from experiments involving the bacterial expression of antibody fragments, all containing one or more variable domains. These molecules include Fab-like molecules (Better et al (1988) Science 240, 1041); Fv molecules (Skerra et al (1988) Science 240, 1038); single-chain Fv (scFv) molecules where the VH and VL partner domains are linked via a flexible oligopeptide (Bird et al (1988) Science 242, 423; Huston et al (1988) Proc. Natl. Acad. Sd. USA 85, 5879) and single domain antibodies (dAbs) comprising isolated V domains (Ward et al (1989) Nature 341, 544). A general review of the techniques involved in the synthesis of antibody fragments which retain their specific binding sites is to be found in Winter & Milstein (1991) Nature 349, 293-299.

By "scFv molecule" is meant a molecule wherein the VH and VL partner domains are covalently linked, e.g. by a flexible oligopeptide.

Fab, Fv, ScFv and dAb antibody fragments can all be expressed in and secreted from E. coli, thus allowing the facile production of large amounts of the said fragments. Whole antibodies, and F(ab')2 fragments are "bivalent". By "bivalent" we mean that the said antibodies and F(ab')2 fragments have two antigen combining sites. In contrast, Fab, Fv, scFv and dAb fragments are monovalent, having only one antigen combining site.

Pharmaceutical Compositions

The invention provides pharmaceutical compositions containing an agent as described herein on combination with a pharmaceutically acceptable excipient, carrier, buffer, stabiliser or other materials well known to those skilled in the art. The term "carrier" will be used to embrace any of these options unless the context requires otherwise. Such materials should be non-toxic and should not interfere with the efficacy of the active ingredient. The precise nature of the carrier or other material may depend on the route of administration, which may be by any suitable route.

The pharmaceutical compositions relating to the invention include those suitable for oral, parenteral inhalation (including fine particle dusts or mists which may be generated by means of various types of metered doses, pressurized aerosols, nebulizers or insufflators), rectal and topical (including dermal, transdermal, transmucosal, buccal, sublingual, and intraocular) administration, although the most suitable route may depend upon, for example, the condition and disorder of the recipient.

The compositions may conveniently be presented in unit dosage form and may be prepared by any of the methods well known in the art of pharmacy. All methods include the step of bringing the active ingredient into association with a pharmaceutical carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Compositions of the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. Various pharmaceutically acceptable carriers and their formulation are described in standard formulation treatises, e.g., Remington's Pharmaceutical Sciences by E. W. Martin. See also Wang, Y. J. and Hanson, M. A., Journal of Parenteral Science and Technology, Technical Report No. 10, Supp. 42:2S, 1988.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The present compounds can, for example, be administered in a form suitable for immediate release or extended release. Immediate release or extended release can be achieved by the use of suitable pharmaceutical compositions comprising the present compounds. The compounds can be formulated, for administration orally, with delivery agents or carriers that facilitate the transport of therapeutic macromolecules and highly charged compounds across cell membranes, especially in the small intestine. Such delivery agents or carriers may in addition inhibit enzymatic degradation of peptides during passage through the gastrointestinal (GI) tract and/or the formulation may include additional agents that protect against such degradation. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The peptide of the invention can also be delivered through the oral cavity by sublingual and/or buccal administration. Moulded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Excipients that can be included are, for instance, proteins, such as human serum albumin or plasma preparations. If desired, the pharmaceutical composition may also contain minor amounts of non-toxic auxiliary substances, such as wetting or emulsifying agents, preservatives, and pH buffering agents and the like, for example sodium acetate or sorbitan monolaurate.

Exemplary compositions for nasal aerosol or inhalation administration include solutions in saline, which can contain, for example, benzyl alcohol or other suitable preservatives, absorption promoters to enhance bioavailability, and/or other solubilizing or dispersing agents such as those known in the art. Conveniently in compositions for nasal aerosol or inhalation administration the compound of the invention is delivered in the form of an aerosol spray presentation from a pressurized pack or a nebulizer, with the use of a suitable propellant, e.g., dichlorodifluoro-methane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated to contain a powder mix of the compound and a suitable powder base, for example lactose or starch. In one specific, non-limiting example, a compound of the invention is administered as an aerosol from a metered dose valve, through an aerosol adapter also known as an actuator. Optionally, a stabilizer is also included, and/or porous particles for deep lung delivery are included (e.g., see U.S. Pat. No. 6,447,743).

Formulations for rectal administration may be presented as a retention enema or a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

A pharmaceutical composition may comprise a dosage from having an enteric coating. An enteric coating is a coating applied to oral medicinal compositions such as tablets, caplet and capsules so as to control absorption so that it takes place in the small intestine. Enteric coatings are typically applied to the surface of dosage forms so that they present a stable surface in the highly acid pH of the stomach, but breakdown rapidly in the relatively more basic environment of the small intestine. Materials used for enteric coatings include fatty acids, waxes, shellac, plastics and plant fibres.

When the present invention is used in the context of delivery of a second therapeutic agent in an oral dosage across the epithelium of the small intestine, an enteric coating may be used if the therapeutic agent would otherwise be degraded in the stomach environment. Such a coating may be especially useful if the second therapeutic agent is irritating to the stomach, if it is acid unstable (for example certain azoles such as esomeprazole are acid unstable), or if the second therapeutic agent is a protein or peptide(for example insulin, GLP-1 or a derivative, or analogue thereof) which might be expected to be degraded by enzymes present in the stomach.

Accordingly, pharmaceutical compositions according to the second aspect of the invention may comprise a solid dosage form having an enteric coating and other aspects of the invention may also utilise or relate to such a coating.

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The agents of the invention are also suitably administered as sustained-release systems. Suitable examples of sustained-release systems of the invention include suitable polymeric materials, for example semi-permeable polymer matrices in the form of shaped articles, e.g., films, or microcapsules; suitable hydrophobic materials, for example as an emulsion in an acceptable oil; or ion exchange resins; and sparingly soluble derivatives of the compound of the invention, for example, a sparingly soluble salt. Sustained-release systems may be administered orally; rectally; parenterally; intracistemally; intravaginally; intraperitoneally; topically, for example as a powder, ointment, gel, drop or transdermal patch; bucally; or as an oral or nasal spray.

Preparations for administration can be suitably formulated to give controlled release of agents of the invention. For example, the pharmaceutical compositions may be in the form of particles comprising one or more of biodegradable polymers, polysaccharide jellifying and/or bioadhesive polymers, amphiphilic polymers, agents capable of modifying the interface properties of the particles of the peptides of the invention. These compositions exhibit certain biocompatibility features which allow a controlled release of the active substance. See U.S. Pat. No. 5,700,486.

A therapeutically effective amount of a peptide or pharmaceutical composition of the invention may be administered as a single pulse dose, as a bolus dose, or as pulse doses administered over time. Thus, in pulse doses, a bolus administration of a peptide or composition of the invention is provided, followed by the elapse of time period followed by a second bolus administration. In specific, non-limiting examples, pulse doses of a compound of the invention are administered during the course of a day, during the course of a week, or during the course of a month.

The pharmaceutical composition may comprise an agent which promotes transit of the agent (or peptide) across the plasma membrane of the target epithelial cell, for example a liposome-forming agent. The presence of such an agent is especially desirable if the agent itself lacks a CPP sequence or suitable chemical modification. However, agents to assist with cell penetration may be present regardless of the presence or absence of such sequences or chemical modifications. Such agents include lipids such as cholesterol, bile acids, cationic polymers and dendrimers. Nanoparticulate formulations may also be employed. See, for example, Wang et al., AAPS J. 2010 December; 12(4): 492-503.

Administration is preferably in a "therapeutically effective amount", this being sufficient to show benefit to the individual. The actual amount administered, and rate and time-course of administration, will depend on the nature and severity of the disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Conditions for Treatment

The agents and compositions described herein may be used for treatment of a disease, disorder or other condition, when administered in conjunction with a suitable therapeutic agent.

The ability to deliver therapeutic agents to discrete epithelial locations would also result in the local delivery to the submucosal space.

The condition may be localised at or near an epithelial surface such that it would benefit from administration of a therapeutic agent via that epithelial surface.

For example, the condition may be a condition of the respiratory tract, including inflammatory conditions asthma or fibrosis, infections of the respiratory tract, a lung disease, or a cancer of the respiratory tract.

The condition may be a condition of the gastrointestinal tract, and particularly a condition that might benefit from directed delivery to the gastrointestinal tract lamina propria and subsequently the hepatic-portal vascular bed. Examples include inflammatory bowel diseases (e.g. Crohn's disease, colitis, coeliac disease), gastrointestinal infections, and cancers of the gastrointestinal tract.

Conditions affecting the liver may also benefit from directed delivery to the hepatic-portal vascular bed via the gastrointestinal tract.

Alternatively the condition may be a systemic condition which would benefit from administration of a therapeutic agent via the respiratory or gastrointestinal tract, such as a cancer, an autoimmune condition (e.g. rheumatoid arthritis), a metabolic condition (e.g. diabetes, whether Type 1 or Type 2), infection by a pathogen (e.g. a microbial infection, such as a bacterial or viral infection, including sepsis), short stature, hypercalcaemia, osteoporosis etc.

The substance to be administered may be any agent which would be helpful for prophylaxis or treatment of such a condition. For example, delivery of insulin or GLP-1 (or other GLP-1 receptor agonists) via the gastrointestinal tract may be particularly useful for treatment of diabetes (Type 1 or Type 2) and other metabolic disorders. Antibiotics (e.g. aminoglycoside antibiotics such as gentamicin) may be useful for treatment of bacterial infections including sepsis, octreotide and other somatostatin analogues may be useful in treatment of growth hormone-producing tumours (e.g. acromegaly), and calcitonin may be useful in treatment of hypercalcaemia or osteoporosis. Chemotherapeutic agents may be administered for treatment of suitable cancers. The skilled person will be aware of numerous other potential applications.

Salts and Solvates

The agents described herein may be provided in the form of a suitable salt, such as pharmaceutically acceptable salts. Suitable salts include those formed with organic or inorganic acids or bases. Pharmaceutically acceptable acid addition salts include those formed with hydrochloric, hydrobromic, sulphuric, nitric, citric, tartaric, acetic, phosphoric, lactic, pyruvic, acetic, trifluoroacetic, succinic, perchloric, fumaric, maleic, glycollic, lactic, salicylic, oxaloacetic, methanesulfonic, ethanesulfonic, p-toluenesulfonic, formic, benzoic, malonic, naphthalene-2-sulfonic, benzenesulfonic, and isethionic acids. Other acids such as oxalic, while not in themselves pharmaceutically acceptable, may be useful as intermediates in obtaining the compounds of the invention and their pharmaceutical acceptable salts. Pharmaceutically acceptable salts with bases include ammonium salts, alkali metal salts, for example potassium and sodium salts, alkaline earth metal salts, for example calcium and magnesium salts, and salts with organic bases, for example dicyclohexylamine and N-methyl-D-glucomine.

Those skilled in the art of organic chemistry will appreciate that many organic compounds can form complexes with solvents in which they are reacted or from which they are precipitated or crystallized. Such complexes are known as "solvates". For example, a complex with water is known as a "hydrate". The present invention provides solvates of compounds of the invention.

Peptide Synthesis

Peptides of the invention may be made by any suitable technique for making peptides, including but not limited to conventional methodology, for example, synthesis from individual amino acids, especially step-wise synthesis using an automatic peptide synthesizer; modification of native peptides; or recombinant manufacturing techniques.

EXAMPLES

Materials and Methods

Peptide Synthesis

Peptides were synthesized by the (Fmoc)-SPPS process using amino acid derivatives obtained from Novabiochem, except for isoleucine, which was obtained from Sigma Aldrich. The first amino acid was coupled to Rink Amide MBHA resin (100-200 mesh; Novabiochem) using N,N'-diisopropylcarbodiimide and 1-hydroxbenzotriazole. Subsequent couplings were carried out on an Activo P-11 peptide synthesizer using PyBOP. Deprotection was carried out using 20% piperidine in dimethylformamide. Peptides were cleaved from the resin using trifluoroacetic acid (TFA), triisopropylsilane, and water (95:2.5:2.5) prior to precipitation in diethyl ether. Crude peptides were purified by HPLC using a Phenomenex Gemini C18 column (250×10 mm, pore size 5 μm) and a gradient mobile phase of water and acetonitrile (both with 0.1% TFA) using a flow rate of 2.5 mL/min. High-resolution time-of-flight mass spectra were obtained on a Bruker Daltonics micrOTOF mass spectrometer using electrospray ionization (ESI) to verify peptide identity. Purified peptides were lyophilized and stored at −20° C.

Caco-2 Cell Culture

An immortalized human intestinal epithelial cell line (Caco-2) was maintained in DMEM/F12 (Gibco, Paisley, UK) supplemented with 10% FBS, 2 mM L-glutamine (Gibco) 100 U/mL penicillin and 100 μg/mL streptomycin (Gibco). Caco-2 cells were seeded at a density of $7\times10^4$/well on Transwell™ (Corning, NY) polyester membrane filters (12 mm diameter, 0.4 μm pore size). Feeding with fresh media (Life Technologies, Paisley, UK) was carried out every second day. Caco-2 monolayers with trans-epithelial electrical resistance (TEER) >350 $\Omega \cdot cm^2$ were used for these studies; such TEER values as measured using fixed paddle electrodes and a voltohmeter (World Precision Instruments, UK), were typically achieved between days 15-18 following seeding on Transwell™ filters.

In Vitro Transport Assay

Apical to basal flux of 10 mg/mL 4 kDa fluorescent dextran (Sigma) was performed to assess PIP peptide impact on paracellular permeability. Apical (200 μL) and basal (500 μL) compartment media were replaced with fresh HBSS and allowed to equilibrate for 30 min when TEER measurements were obtained to ensure monolayer integrity. After apical application of the fluorescent dextra the basal compartment volume was collected at set times (typically 0, 15, 30 60, 90, 120 and 180 min) and replaced with fresh HBSS each time. Apical and basal compartment fluorescence was determined using a Fluorostar Omega microplate reader (BMG Labtech, Ortenburg, Germany). After 3 h, the apical compartment fluorescent dextran/peptide solution was removed and replaced with PBS and TEER values were recorded for a further 30 min to monitor monolayer recovery. TEER values were calculated by subtracting blank filter readings and normalized as a percentage of the initial TEER value for that monolayer.

Animals

Male Wistar rats weighing 250-300 g were used in in vivo experiments. Rats were bred in house at the University of Bath. Rats were kept on a 12/12-hour light dark cycle. Experiments were conducted at the midpoint of the light cycle±3 hours. Rats had ad lib access to food and water throughout housing up to the beginning of experimental procedures. Following experimental procedures rats were euthanised by exposure to increasing concentration of $CO_2$. In Vivo Intraluminal Injection (ILI)

Rats were anaethetised using 5% inhaled isoflurane. Once anaesthesia was achieved, rats were transferred to a nose cone to maintain anaesthesia. A 2-cm incision was used to gain access to the abdominal cavity. A sufficient segment of the intestine was removed to locate the jejunum and a 25 G needle was used to inject the test substance directly into its lumen. A permanent marker was used to identify the mesentery adjacent to the injection site for tissue collection at study termination.

Collection of Serum Samples for LCMS/MS

Blood samples (100 μL) were collected from either the tail vein or the portal vein into 1.5 mL Eppendorf tubes and allowed to clot at room temperature for 20 min. Serum collected from clotted blood after centrifugation at 2000×g for 10 min was mixed with acetonitrile in a 1:3 ratio and left at 4° C. overnight to precipitate proteins. Samples were centrifuged at 2000×g for 10 min, with the supernatant being collected and analysed by LCMS/MS.

In Vivo Gentamicin Transport

Rats were administered 10 mg/kg gentamicin by ILI with or without 20 mM of a PIP250 series peptide. Blood samples collected from 15 to 90 min post-IL were analysed for gentamicin. In separate experiments, PIP250 series peptides were injected alone, followed by injected of gentamicin alone after a delay of 30 or 60 min. Blood samples were collected and analysed as previously described.

LCMS/MS Analysis of Serum Concentration of Gentamicin

Samples were analysed using an Agilent 6545 quadrupole time-of-flight LC/MS instrument. 10 μL of gentamicin samples were injected into a C18 reversed-phase HPLC column and detected at 202 nm. Samples were ionised by electrospray ionisation and gentamicin in the samples was confirmed by mass/charge analysis. Quantification was carried out by Agilent Mass Hunter Quant Software.

Western Blotting

Lysates of Caco-2 monolayers prepared using 200 μL RIPA buffer along with 10 μL protease and phosphatase inhibitors per well were placed in 1.5 mL Eppendorf tubes and centrifuged at 4000×g for 10 min with supernatants being removed and stored at −80° C. until separation using a 12% SDS-PAGE gel. Protein samples were mixed 1:1 with loading buffer and denatured by heating at 95° C. for 5 min with 20 μL being loaded for analysis. Separated proteins were transferred onto a nitrocellulose membrane at 30 V for 75 min. Membranes were blocked with 5% bovine serum albumin in TBS-T for 2 h prior to an overnight incubation at 4° C. with primary antibodies diluted in TBS-T. Membranes were thrice washed with TBS-T and then incubated with fluorescent-tagged secondary antibodies at room temperature for 2 h. Membranes were thrice washed with TBS-T and analysed using a Licor imaging system.

Binding Assay

His-tagged PP1 diluted in PBS-T was incubated in nickel coated wells for 1 hour and washed three times with PBS-T. Wells were incubated with increasing concentrations of biotinylated PIP peptides or amino acids 1-299 of MYPT1. Wells were washed again three times with PBS-T and incubated with streptavidin conjugated to Alexa Fluor 488 for 1 hour. Wells were washed as previously and the plate was read for fluorescence (Ex:480 nm, Em: 510 nm).

The binding assay with MYPT1 was repeated in the presence of increasing concentrations of PIP peptides to determine the competition between MYPT1 and the peptides.

Data Processing

Graphs and statistical analysis were performed using GrapPad Prism software with one-way ANOVA and Bonferroni's post-test being used.

Results

Rationale for Peptide Modifications

PIP250 was designed to inhibit the interaction between PP1 and MYPT1. It was based on the PP1 binding motif on MYPT1, [35]KVKF[38], and flanking amino acids. The binding motif was retained and adjacent negatively charged aspartic acid residues were replaced with positively charged arginine residues to make the peptide resemble a cell penetrating peptide [23]. A strategy where the L-amino acid sequence was reversed and replaced with D-amino acids (i.e. retroinverso) was used to increase peptide stability while maintaining order and orientation of the side chains. Substitutions were made to the retroinverso sequence based on amino acids expected to be involved in the interaction with PP1. For example, Phe-38 and Val-36 on MYPT1 associate with a hydrophobic pocket on PP1 during binding. These residues are analogous to Phe-P3 and Val-P5 on PP1 and the focus of the current study. Phenylalanine and valine are amino acids with hydrophobic side chains. This property may be involved in the binding of these amino acids to the PP1 hydrophobic pocket. To test this hypothesis, negatively charged aspartic acid was used to replace Phe-P3 or Val-P5 for peptides PIP253 and PIP254, respectively. To assess whether these amino acids are specifically required, rather than just their hydrophobic properties, alanine was also used to replace Phe-P3 or Val-P5 for peptides PIP251 and PIP252 respectively (Table 1).

TABLE 1

| Sequences of PIP250 series peptides and rationale for modifications | | |
| --- | --- | --- |
| Peptide | Sequence | Rationale |
| PIP250 | H-rrfkvktkkrk-NH2 | Parent peptide |
| PIP251 | H-rrakvktkkrk-NH2 | Specificity of residue binding |
| PIP252 | H-rrfkaktkkrk-NH2 | Specificity of residue binding |
| PIP253 | H-rrdkvktkkrk-NH2 | Physicochemical properties of binding |
| PIP254 | H-rrfkdktkkrk-NH2 | Physicochemical properties of binding |

Effect of Phe-P3 or Val-P5 Modifications on TEER

In all cases, these peptides were tested at 5 mM applied to the apical surface of confluent, polarized Caco-2 monolayers. PIP251, where Phe-P3 is replaces by an alanine reduced TEER to 62.7%, slightly but insignificantly less than the effect on TEER observed for PIP250 (FIG. 1A). In comparison, PIP253, where Phe-P3 is replace with a glutamic acid, only reduced TEER to 88% of baseline that was statistically different from PIP250 (FIG. 1A). Replacement of Val-P5 with an alanine residue (PIP252) showed a reduction in TEER to 66% of baseline, providing a similar result to the original PIP250; replacement of Val-P5 with aspartic acid (PIP254), however, resulted in a peptide that reduced TEER to only 85% of baseline (FIG. 1B).

Effect of Phe3 or Val5 Changes on Permeability and pMLC Levels

Figure 2:
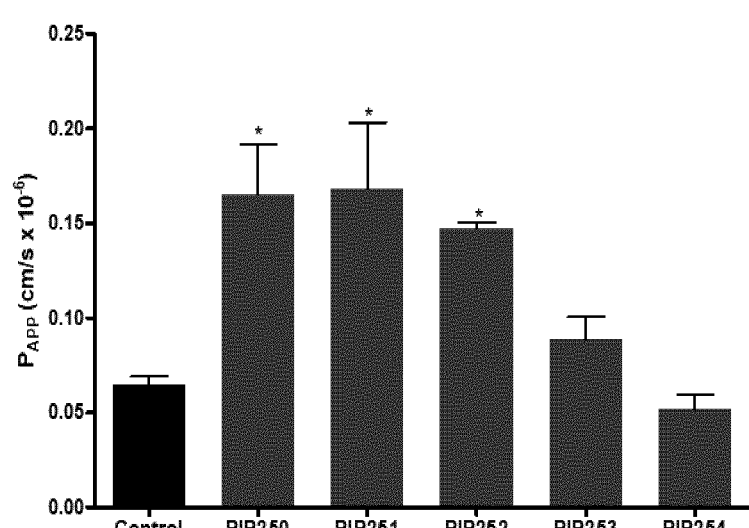
FIG. 2. Effect of PIP250-254 series, tested at 5 mM, on A) apparent permeability (PAPP) of 4 kDa fluorescent dextran across Caco-2 monolayers and B) ratio of phosphorylated myosin light chain (pMLC) to total MLC. Data are means±SD (n=3). *$p < 0.05$ compared to control with unpaired, two-tailed t-test.
Figure 2:
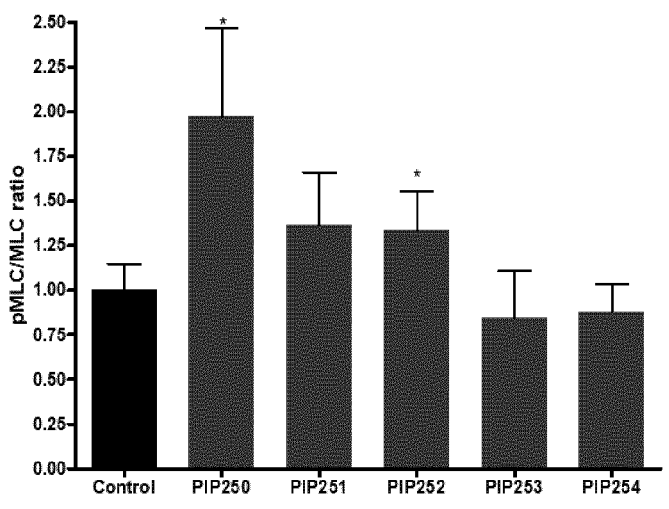

To assess the impact of TEER changes induced by the PIP250-254 series on paracellular solute movement, the apparent permeability ($P_{APP}$) of 4 kDa fluorescent dextran across Caco-2 cell monolayers was determined (FIG. 2A). Untreated Caco-2 monolayers had a PAPP of $0.60 \times 10^{-5}$ cm/s. Apical application of PIP250 increased $P_{APP}$ to $1.65 \times 10^{-5}$ cm/s. PIP251 increased it $1.68 \times 10^{-5}$ cm/s and PIP252 to $1.47 \times 10^{-5}$ cm/s. $P_{APP}$ after PIP253 application was $0.87 \times 10^{-5}$ cm/s and after PIP254 application it was $0.51 \times 10^{-5}$ cm/s. An unpaired, two-tailed t-test showed that the effect of PIP250 (p=0.006), PIP251 (p=0.006) and PIP252 (p=0.005) were significantly different from untreated control; PIP253 and PIP254 do not show any significant differences from the control.

Following application of PIP250 to Caco-2 monolayers, the ratio of pMLC to MLC was significantly increased compared to untreated (control) monolayers that were treated identically (FIG. 2B). Both PIP251 and PIP252 treatments also increased the ratio of pMLC to MLC, however to a lesser extent than the parent PIP250. PIP253 and PIP254 did not significantly increase the ratio of pMLC to MLC.

Recovery following Washout is affected by Phe3 or Val5 Changes

Figure 3:
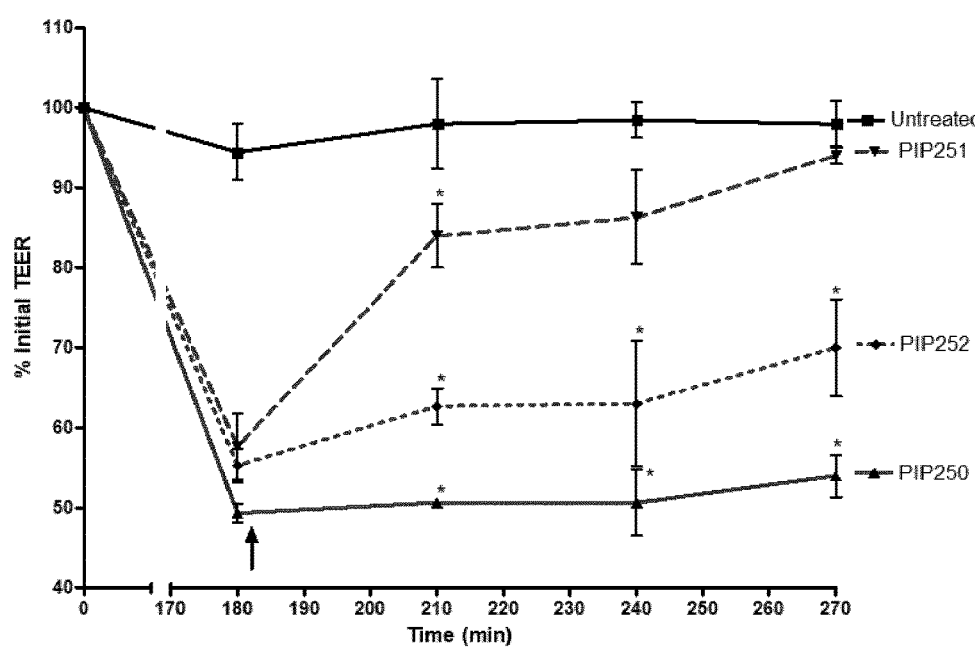
FIG. 3. Recovery of A) trans-epithelial electrical resistance (TEER) of Caco-2 monolayers and B) apparent permeability (PAPP) of 4 kDa fluorescent dextran across Caco-2 monolayers following washout of PIP250, PIP251, or PIP252. Caco-2 monolayers were treated by apical addition of 5 mM of test peptide for 180 min and then monitored for TEER reading over the next 90 min or examined for PAPP at the end of that period. ↑ Point where peptides were washed off Data are means±SD (n=3). *$p < 0.05$ compared to control with unpaired, two-tailed t-test.
Figure 3:
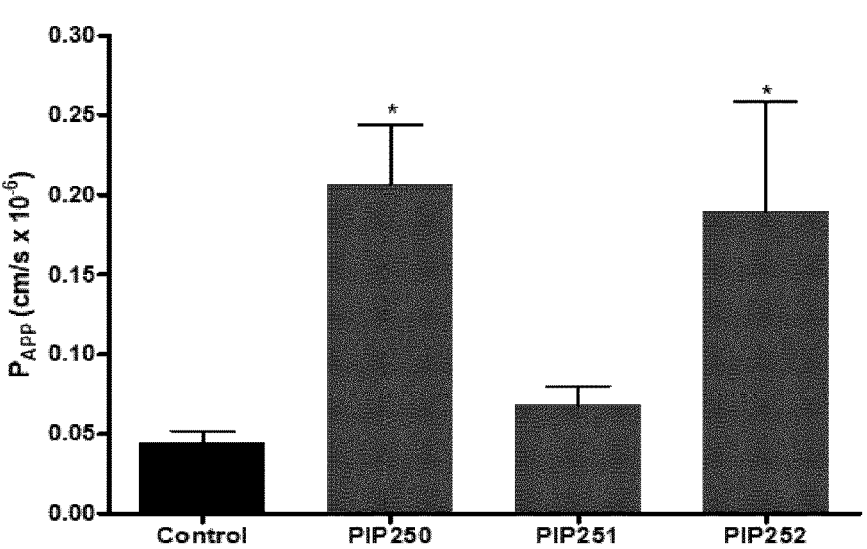

Caco-2 monolayers were treated for 180 min with 5 mM of PIP250, PIP251, or PIP 252 and then monitored for their recovery of TEER following washout (FIG. 3A). PIP250-treated Caco-2 monolayers had ~50% of their initial TEER value at the time of washout; TEER levels following washout failed to recover by 90 min post washout. Specifically, TEER was 49% of initial baseline and 90 minutes after washing it was 54% for PIP250. By comparison, PIP251 reduced TEER to 58% of baseline and after 90 min of recovery it increased to 94%. By this point it was no longer statistically different from baseline. PIP252 reduced TEER to 55% of baseline and 90 min after washout it had slightly recovered to 70% of baseline but remained statistically different from baseline. Additionally, the $P_{APP}$ of 4 kDa fluorescent dextran across Caco-2 monolayers at 90 min following washout of PIP250 peptides was examined and compare to that for PIP251 and PIP252 (FIG. 3B). Control wells had a $P_{APP}$ of $0.05 \times 10^{-6}$ cm/s. $P_{APP}$ for PIP250 and PIP252 wells were still statistically different from control, at 0.21 and $0.19 \times 10^{-6}$ cm/s respectively. PAPP for PIP251 wells, however, was not statistically different from control at $0.07 \times 10^{-6}$ cm/s. These results for recovery of modified $P_{APP}$ and TEER suggested that while PIP250, PIP251, and PIP252 comparably decreased TEER and enhanced paracellular permeability, the action of PIP251 were more rapidly reversible.

Enhancement of Gentamicin Absorption In Vivo

Figure 4:
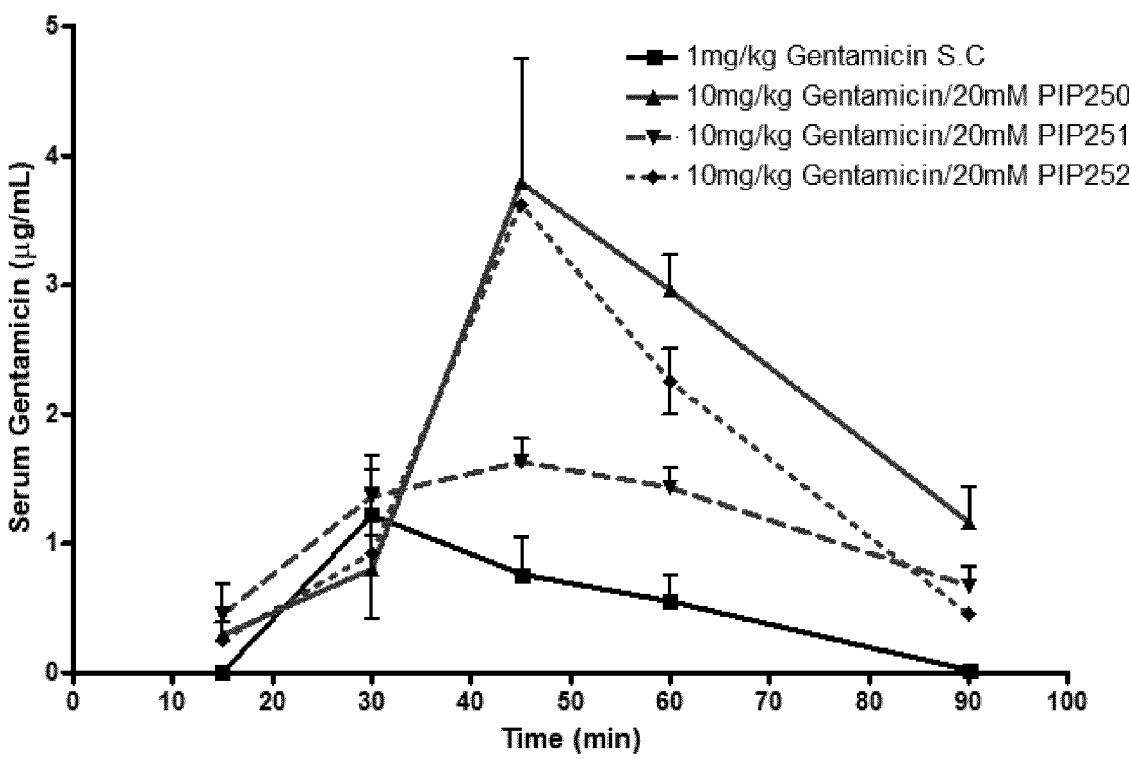
FIG. 4. Serum concentration of gentamicin following intraluminal injection with PIP250 series. Data are means±SD. n=3.

Gentamicin is a water soluble antibiotic of 478 Da with low oral bioavailability. Indeed, intraluminal injection (ILI) of gentamicin alone into the jejunum of rats did not results in detectable serum levels (data not shown). Gentamicin co-administered with PIP peptides PIP250, PIP251, or PIP252 by ILI all showed increased gentamicin serum concentration with $T_{MAX}$ (at ~45 minutes (FIG. 4). Gentamicin $C_{MAX}$ (was 3.79 µg/mL after co-injection with PIP250, 1.63 µg/mL after co-injection with PIP251, and 3.62 µg/mL after co-injection with PIP252.

Gentamicin Absorption after Delayed Injection Following PIP Peptide Injection

Figure 5:
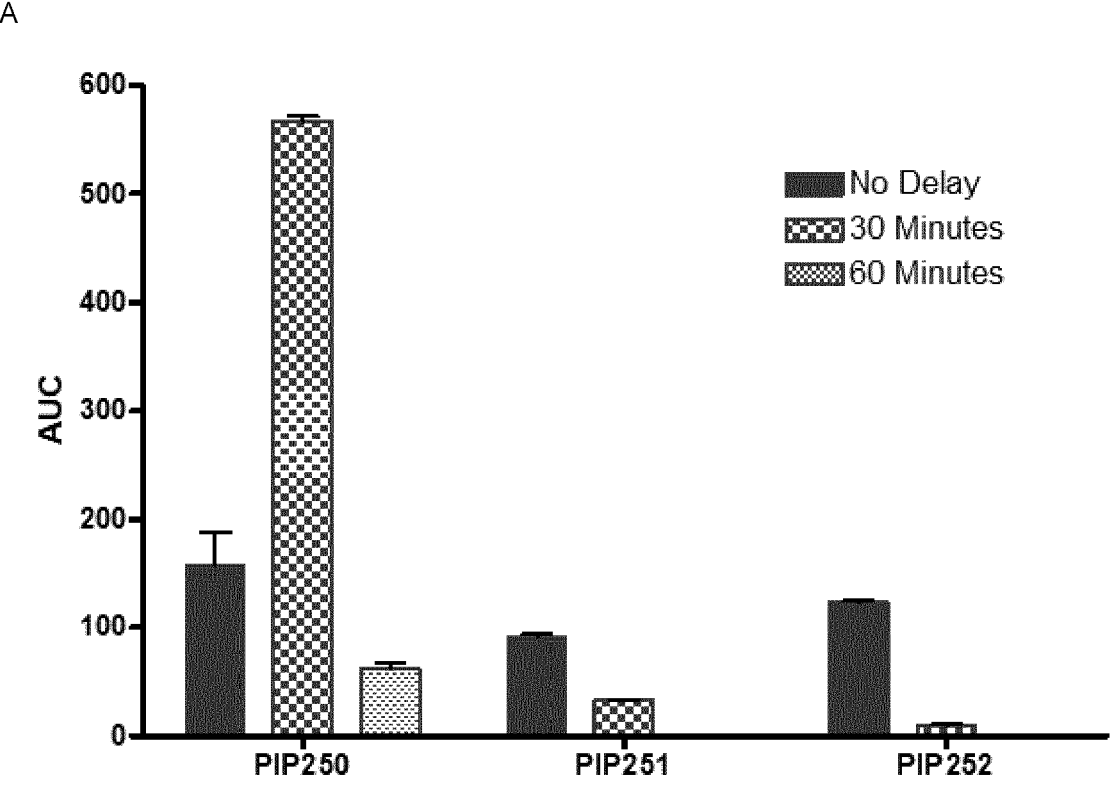
FIG. 5. Serum gentamicin concentration following delayed intraluminal injection after PIP250 series peptide injection. A) Summary of AUC calculated from the other graphs. B) Gentamicin concentration following injection with 0, 30 or 60 minute delay after PIP250 injection. C) Gentamicin concentration following injection with 0, 30 or 60 minute delay after PIP251 injection. D) Gentamicin concentration following injection with 0, 30 or 60 minute delay after PIP252 injection. Data are means+SD. n=3.
Figure 5:
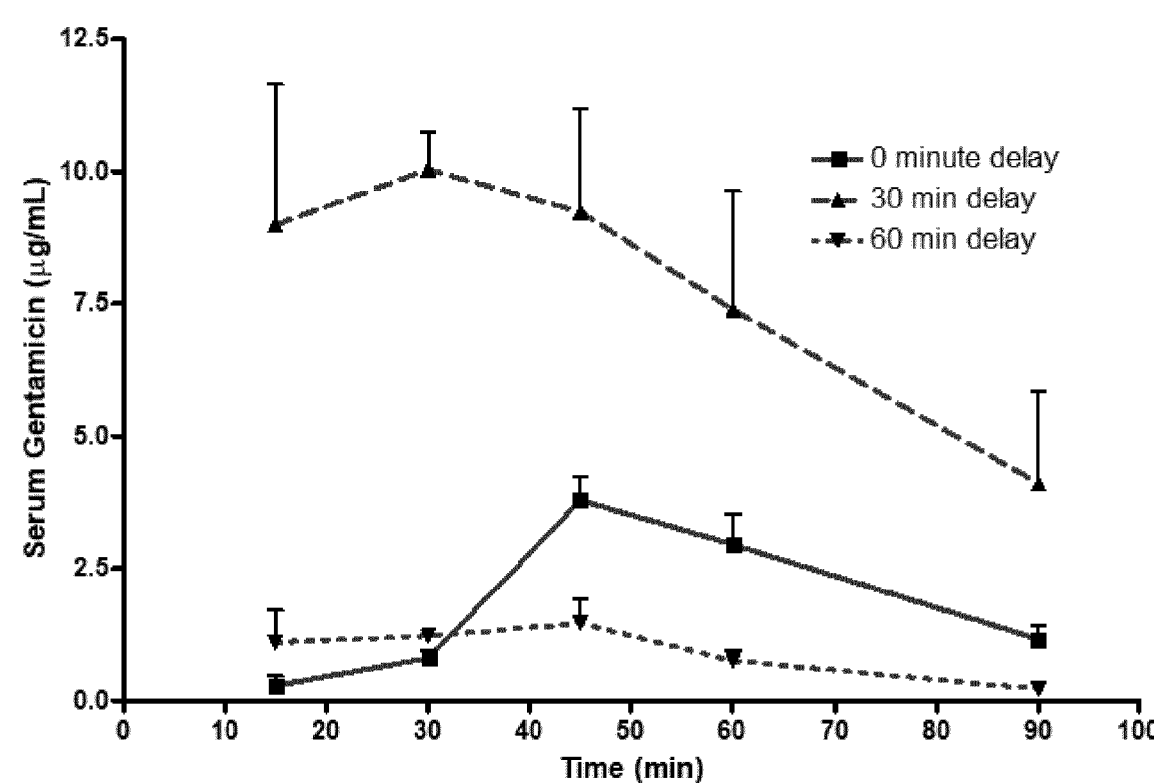
Figure 6:
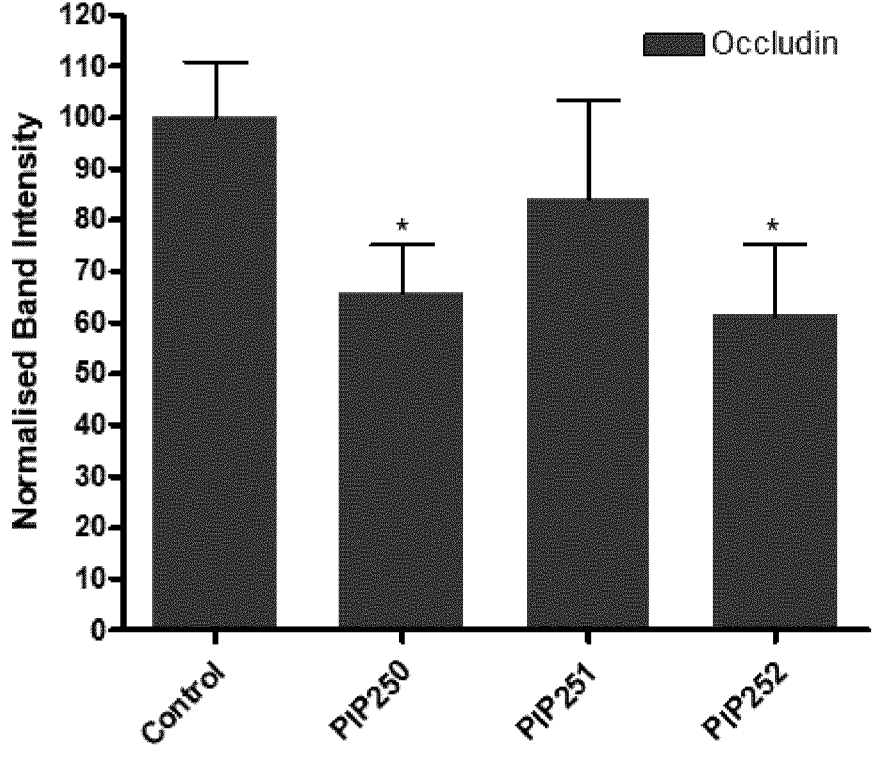
FIG. 6. Band intensity measured from western blots for occludin in lysates from Caco-2 monolayers treated with PIP peptides. Data are normalised so the control=100. Data are means+SD. n=3 *$p < 0.05$ compared to control in two-tailed un-paired t-test.

Since epithelial barrier properties recovered more rapidly after the in vitro withdrawal of PIP251 compared to PIP250 and PIP252, a series of studies were performed to examine the durability of the actions of these peptides in vivo by comparing the extent of gentamicin absorption following intraluminal injection 30 or 60 minutes after PIP peptides, compared with co-injection. First, the overall AUC values calculated from the pharmacokinetic profiles are presented for comparison (FIG. 5A). Co-injection of PIP250 and gentamicin gave an AUC of 155 µg/mL·min and gentamicin 30 or 60 minutes after PIP250 gave 584 µg/mL·min and 68.6 µg/mL·min respectively. Co-injection of PIP251 and gentamicin gave an AUC of 97.7 µg/mL·min and gentamicin 30 after PIP251 gave 32.9 µg/mL·min. Co-injection of PIP252 and gentamicin gave an AUC of 127.4 µg/mL·min and gentamicin 30 after PIP252 gave 8.6 µg/mL·min. When injected 30 minutes after PIP250, gentamicin concentration is higher than following co-injection, with a $C_{MAX}$ (of 10.03 µ/mL compared to 3.79 µg/mL (FIG. 5B). When injected 60 minutes after PIP250, $C_{MAX}$ (of gentamicin decreases to 1.46 µg/mL. When injected 30 minutes after PIP251, gentamicin concentration is lower than following co-injection, with a $C_{MAX}$ (of 0.64 µg/mL compared to 1.63 µg/mL (FIG. 5C). When injected 30 minutes after PIP252, gentamicin concentration is also lower than following co-injection, with a $C_{MAX}$ (of 0.19 µg/mL compared to 3.79 µg/mL (FIG. 5D).

Alteration of Tight Junction Protein Levels

Polarized Caco-2 monolayers treated with PIP250 or PIP252 for 90 min significantly reduced the level of occludin to 65.8% and 61.4% of control levels, respectively. PIP251 treatment reduced occludin to 84.1% compared to control, though this was not statistically significant.

Binding of Peptides to Protein Phosphatase 1

Figure 7:
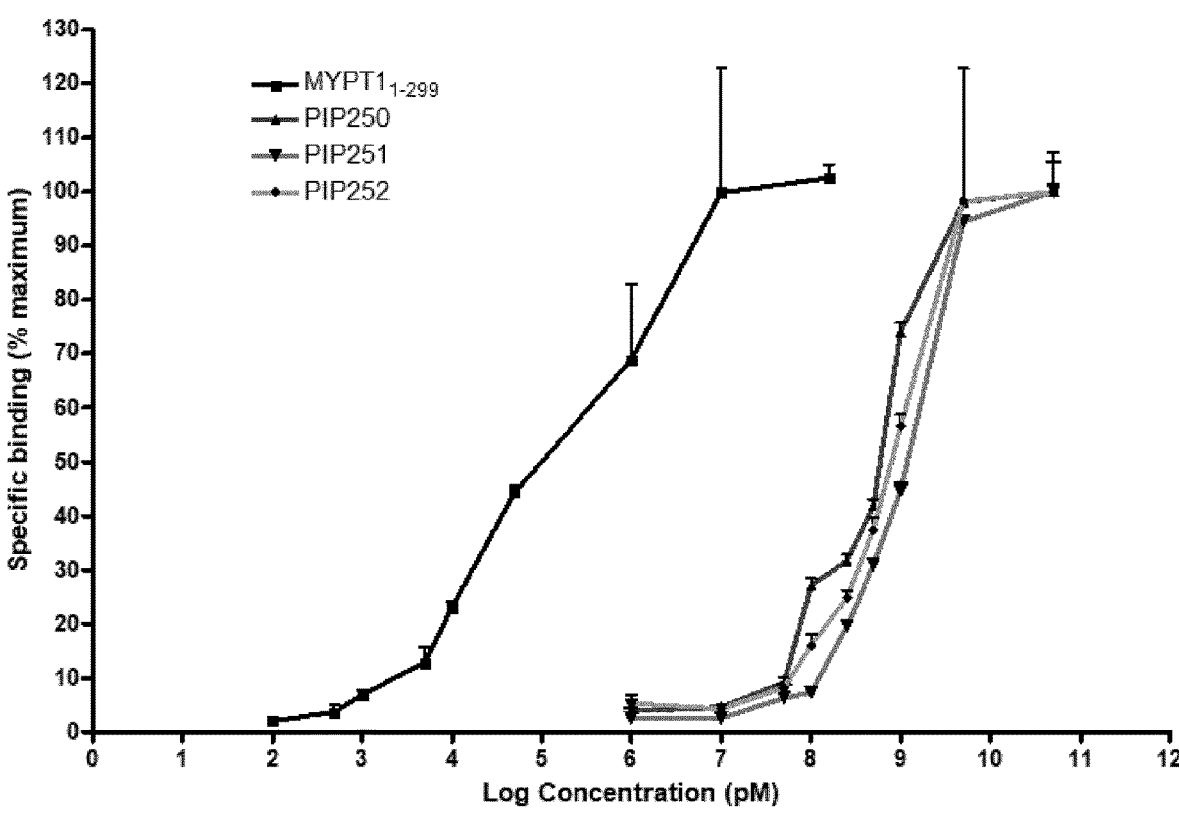
FIG. 7. Binding of PIP peptides to PP1

Peptide PIP250 was designed to bind to PP1 and therefore inhibit binding of MYPT1 and PP1 to form MLCP. To verify that PIP250 binds PP1, and to assess the effects of single amino acid modifications on binding affinity, we performed a binding curve assay for the peptide/protein interaction. His-tagged PP1 was immobilised on nickel coated plates and incubated with biotinylated peptides, which were detected with fluorescently labelled streptavidin. The binding curves for peptides binding to PP1 are shown in FIG. 7. PIP250 bound to PP1 with a calculated $K_D$ of 610 µM. Substitution of valine or phenylalanine reduced binding affinity without complete loss of binding. Calculated $K_D$ values for PIP251 (Phe→Ala) and PIP252 (Val→Ala) were 1282 and 724 µM respectively. MYPT$_{1-299}$ binding to PP1 was also assessed in the same assay and had a significantly higher binding affinity with a $K_D$ of 49 nM.

Figure 8:
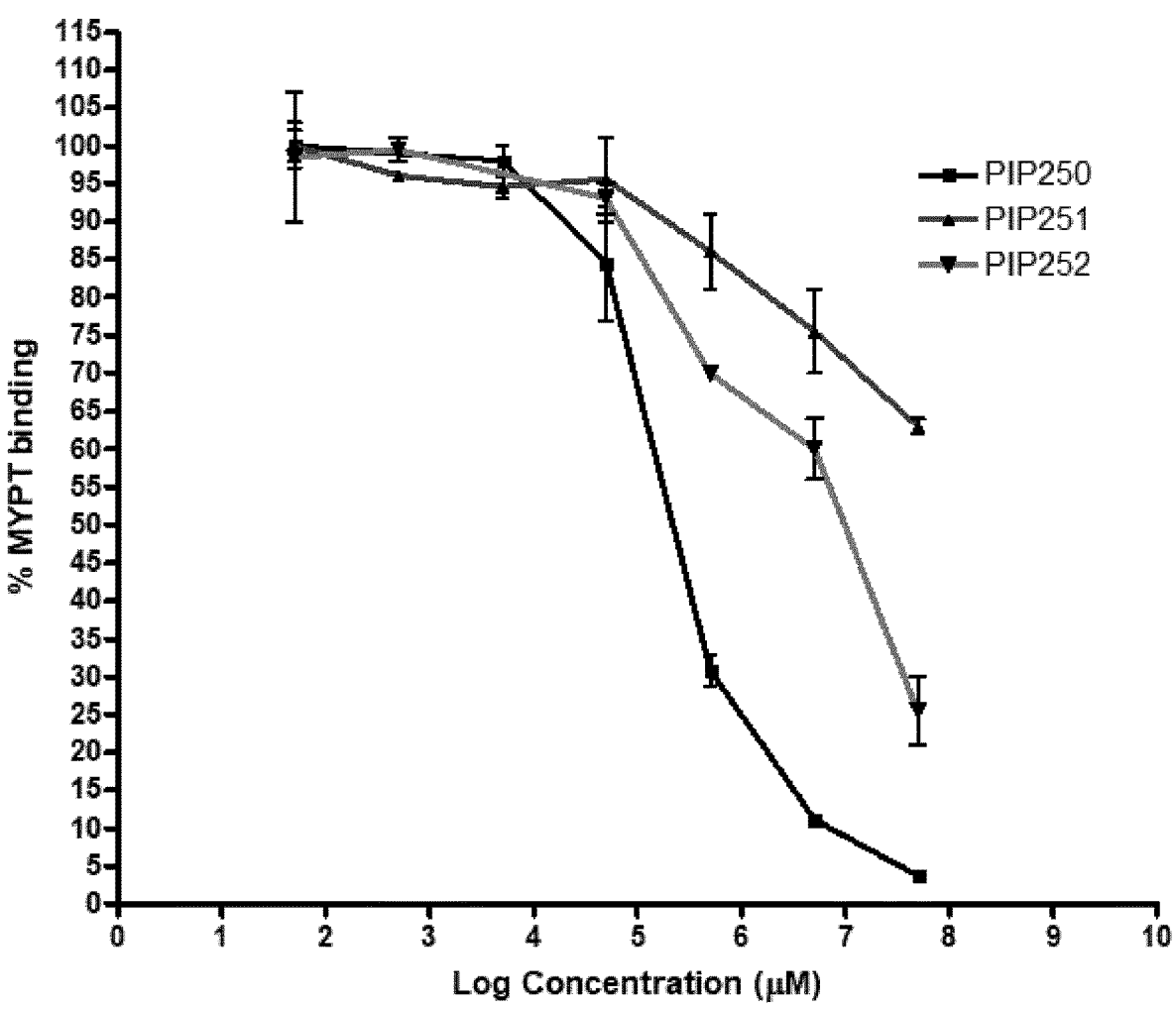
FIG. 8. Inhibition of MYPT1 binding to PP1 by PIP peptides.

To assess if peptide binding to PP1 was sufficient to inhibit MYPT1 binding, the MYPT1/PP1 binding assay was repeated with increasing concentrations of the PIP peptides. The inhibition of MYPT1 binding by the peptides is shown in FIG. 8. PIP250 inhibited the binding of MYPT1 to PP1 in a dose dependent manner. The $K_I$ for PIP250 was calculated as 155 µM.

TABLE 1

| $K_D$ values for PIP or MYPT1 binding to PP1 derived from binding curves | |
| --- | --- |
| Peptide/Protein | $K_D$ (µM) |
| PIP250 | 610 |
| PIP251 | 1282 |
| PIP252 | 724 |
| MYPT1$_{1-299}$ | 0.05 |

Discussion

The results of experiments with PIP250 are consistent with previous data for this peptide [20]. The data also show that substitution of key amino acid residues affects the activity of the peptide in altering the phosphorylation state of MLC and increasing the permeability of Caco-2 monolayers. Both Phe3 and Val5 appear to be important for the peptide activity. Replacing either of these hydrophobic amino acids with an amino acid with a charged, hydrophilic side chain prevents the effects of the peptide on the monolayers and pMLC. However, replacing these residues with another hydrophobic residue has a small or no effect on the peptide's actions on the monolayers, and a modest reduction in the peptide's increase of pMLC. This suggests that the hydrophobic nature of these residues is the important factor in the association with MLCP.

PIP251 and PIP252, where the amino acids are changed but the hydrophobic properties are retained, have similar effect on Caco-2 permeability, but a slightly reduced effect on MLC phosphorylation. This suggests that the hydrophobic side chain is sufficient for the peptide to inhibit MLCP but is slightly reduced in effectiveness. The lower increase in pMLC does not appear to significantly affect PIP-mediated permeability in vitro. However, substituting the phenylalanine with an alanine appears to significantly increase the rate of recovery of the monolayers after the peptide is washed off, suggesting a weaker binding affinity. One hour after washing off, monolayers that had been treated with PIP250 still showed a significantly increased $P_{APP}$ and reduced TEER compared to the control. In contrast, monolayers that had been treated with PIP251 had returned to the same $P_{APP}$ and TEER as the control. There was also some recovery in TEER following PIP252 being washed off, though this did not correspond to a reduction in $P_{APP}$. It is possible that while all three peptides interact with MLCP in a similar way, the interaction of PIP250 with the enzyme is stronger, meaning that it stays associated for longer after it is washed off. Potentially, a weaker interaction between PIP251 and MLCP could result in a more rapid dissociation, and a quicker return to baseline physiological conditions. The results suggest that PIP252 is somewhere in between PIP250 and PIP251 in terms of the dissociation after washing. Indeed, the data from binding assays between the peptides and PP1 supports this hypothesis. Each peptide binds to PP1 with PIP250 binding with the highest affinity, followed by PIP252 then PIP251. Most significantly, the peptides are able to inhibit binding of the first 299 amino acid fragment of MYPT1 to PP1. Again, PIP250 has the greatest efficacy in inhibiting this interaction with PIP252 being greater than PIP251. The rationale for the design of these peptides is that they inhibit the binding of MYPT1 to PP1 to make MLCP, so the ability of the peptides to displace MYPT1 is key to their action. By displacing MYPT1 from PP1 with a lower efficacy, it appears that modified peptides PIP252 and PIP251 may have a more transient effect.

When tested in vivo, PIP250 promoted delivery of gentamicin into the blood following co-injection into the jejunum. PIP251 also promoted delivery of gentamicin, however whereas the in vitro data shows very little decrease in effect of PIP251 compared to PIP250, in vivo the gentamicin levels are noticeably lower with an AUC of 90.5 µg/mL·min compared to 155 µg/mL·min for PIP250. Although lower than PIP250, PIP251 mediated gentamicin absorption still compares well to subcutaneous gentamicin. Co-injection of PIP252 with gentamicin delivered more gentamicin than PIP251, with an AUC of 127.4 µg/mL·min. Using the AUC and the doses of gentamicin administered, the relative bioavailability ($F_{REL}$) can be calculated using the formula:

$$F_{REL}=((AUC_{ILI} \times D_{SC})/(AUC_{SC} \times D_{ILI})) \times 100$$

This gives an $F_{REL}$ of 36.5% for PIP250, 21.3% for PIP251 and 31.0% for PIP252.

After 30 minutes, the serum concentration of gentamicin is similar for all three peptides tested in vivo, with all showing a moderate increase in gentamicin. Then between 30 and 45 minutes, there is a rapid increase in concentration in animals injected with gentamicin and PIP250 or PIP252, but not PIP251. This suggests that there are two stages to the increase in permeability induced by PIP250 and PIP252, and that the second stage is not present with PIP251. This correlates with the effect the peptides have on occludin levels in vitro. PIP250 and PIP252 significantly reduce the amount of occludin detected in caco-2 cells after treatment. PIP251 appears to reduce occluding to a lesser extent. This suggests that occludin down-regulation could be responsible for the greater increase in gentamicin concentration with PIP250 and PIP252. As PIP251 and PIP252 show similar levels of effect of pMLC but significant differences in occludin levels, it suggests that a secondary mechanism of action is involved.

Following a 30-minute delay between PIP250 and gentamicin injection, the amount of gentamicin in the blood is significantly higher than with co-injection. This suggests that the effect PIP250 has is still increasing at 30 minutes. With the same delay between PIP251 and gentamicin, there is a lower amount of gentamicin in the blood compared to co-injection. Following a 60-minute delay between PIP250 and gentamicin injection, there is still gentamicin absorption higher than PIP251 with a 30-minute delay. These data suggest that PIP250 is having an effect for a longer time after injection than PIP251 and PIP252, which is consistent with the in vitro data showing an improved recovery profile for PIP251 and PIP252 compared to PIP250. Interestingly, though PIP252 only showed partial recovery in vitro, it shows the best recovery in vivo.

To be used clinically, a permeation enhancer would require a transient action that reliably returns to physiological conditions, so the increase in permeability is limited to the time of the drug delivery without any prolonged or lasting impact on the integrity of the epithelium. The data suggest that PIP251 and PIP252 enhance the absorption of gentamicin. PIP251 appears to be a lot less effective than PIP250 but has a shorter recovery time to resting conditions. PIP252 enhances delivery of gentamicin to similar levels as PIP250, but showed improved recovery after 30 minutes, and thus appears to be slightly better than PIP251.

Taken together, these data show that PIP252 has a similar profile of enhancing permeability to PIP250 but has a significantly better recovery time. This makes it the most promising candidate as a transient permeation enhancer out of the peptides that have been tested.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

REFERENCES

A number of publications are cited above in order to more fully describe and disclose the invention and the state of the art to which the invention pertains. Full citations for these references are provided below. The entirety of each of these references is incorporated herein.

1. Anderson, J. M. and C. M. Van Itallie, *Physiology and function of the tight junction.* Cold Spring Harb Perspect Biol, 2009. 1(2): p. a002584.

2. Zihni, C., et al., *Tight junctions: from simple barriers to multifunctional molecular gates.* Nature Reviews Molecular Cell Biology, 2016. 17(9): p. 564-580.

3. Maher, S., R. J. Mrsny, and D. J. Brayden, *Intestinal permeation enhancers for oral peptide delivery.* Advanced Drug Delivery Reviews, 2016. 106: p. 277-319.

4. Wong, V. and B. M. Gumbiner, *A synthetic peptide corresponding to the extracellular domain of occludin perturbs the tight junction permeability barrier.* Journal of Cell Biology, 1997. 136(2): p. 399-409.

5. Fasano, A., et al., *The enterotoxic effect of zonula occludens toxin on rabbit small intestine involves the paracellular pathway*. Gastroenterology, 1997. 112(3): p. 839-846.

6. Freedman, J. C., A. Shrestha, and B. A. McClane, *Clostridium perfringens Enterotoxin: Action, Genetics, and Translational Applications*. Toxins, 2016. 8(3).

7. Krug, S. M., et al., *Angubindin-1, a novel paracellular absorption enhancer acting at the tricellular tight junction*. Journal of Controlled Release, 2017. 260: p. 1-11.

8. Krug, S. M., et al., *Sodium caprate as an enhancer of macromolecule permeation across tricellular tight junctions of intestinal cells*. Biomaterials, 2013. 34(1): p. 275-282.

9. Lemmer, H. J. R. and J. H. Hamman, *Paracellular drug absorption enhancement through tight junction modulation*. Expert Opinion on Drug Delivery, 2013. 10(1): p. 103-114.

10. Kondoh, M. and K. Yagi, *Tight junction modulators: Promising candidates for drug delivery*. Current Medicinal Chemistry, 2007. 14(23): p. 2482-2488.

11. McCartney, F., J. P. Gleeson, and D. J. Brayden, *Safety concerns over the use of intestinal permeation enhancers: A mini-review*. Tissue Barriers, 2016. 4(2).

12. Shen, L., et al., *Myosin light chain phosphorylation regulates barrier function by remodeling tight junction structure*. J Cell Sci, 2006. 119(Pt 10): p. 2095-106.

13. Turner, J. R., et al., *Physiological regulation of epithelial tight junctions is associated with myosin light-chain phosphorylation*. Am J Physiol, 1997. 273(4): p. C1378-85.

14. Cunningham, K. E. and J. R. Turner, *Myosin light chain kinase: pulling the strings of epithelial tight junction function*. Ann N Y Acad Sci, 2012. 1258: p. 34-42.

15. Terrak, M., et al., *Structural basis of protein phosphatase 1 regulation*. Nature, 2004. 429(6993): p. 780-4.

16. Eto, M., *Regulation of Cellular Protein Phosphatase-1 (PP1) by Phosphorylation of the CPI-17 Family, C-kinase-activated PP1 Inhibitors*. Journal of Biological Chemistry, 2009. 284(51): p. 35273-35277.

17. Pinheiro, A., et al., *Structural signature of the MYPT1-PP1 interaction*. J Am Chem Soc, 2011. 133(1): p. 73-80.

18. Tanaka, J., et al., *Interaction of myosin phosphatase target subunit 1 with the catalytic subunit of type 1 protein phosphatase*. Biochemistry, 1998. 37(47): p. 16697-16703.

19. Tóth, A., et al., *Study of the subunit interactions in myosin phosphatase by surface plasmon resonance*. Eur J Biochem, 2000. 267(6): p. 1687-97.

20. Taverner, A., et al., *Enhanced paracellular transport of insulin can be achieved via transient induction of myosin light chain phosphorylation*. Journal of Controlled Release, 2015. 210: p. 189-197.

21. Almansour, K., et al., *Mechanistic studies of a cell-permeant peptide designed to enhance myosin light chain phosphorylation in polarized intestinal epithelia*. J Control Release, 2018. 279: p. 208-219.

22. Almansour, K., et al., *An intestinal paracellular pathway biased toward positively-charged macromolecules*. J Control Release, 2018. 288: p. 111-125.

23. Kristensen, M. and H. M. Nielsen, *Cell-Penetrating Peptides as Carriers for Oral Delivery of Biopharmaceuticals*. Basic Clin Pharmacol Toxicol, 2016. 118(2): p. 99-106.

For standard molecular biology techniques, see Sambrook, J., Russel, D. W. *Molecular Cloning, A Laboratory Manual*. 3 ed. 2001, Cold Spring Harbor, New York: Cold Spring Harbor Laboratory Press

The invention claimed is:

1. An agent capable of increasing epithelial permeability, wherein the agent comprises a peptide of no more than 15 amino acids in length, said peptide comprising a core sequence of Formula I:

x3-k-x5-k       (Formula I)

wherein
(i) x3 is D-Phe and
x5 is selected from D-Ala, D-Leu and Gly; or
(ii) x3 is D-Ala and x5 is selected from D-Val, D-Ala, D-Leu and Gly.

2. The agent according to claim 1, wherein the peptide has a core sequence of Formula II:

x3-k-x5-ktk      (Formula II)

wherein
(i) x3 is D-Phe and x5 is selected from D-Ala, D-Leu and Gly; or
(ii) x3 is D-Ala and x5 is selected from D-Val, D-Ala, D-Leu and Gly.

3. The agent according to claim 1, wherein the agent is capable of crossing the plasma membrane of an epithelial cell.

4. The agent according to claim 3, wherein the peptide comprises one or more additional sequence(s) capable of mediating transit across the plasma membrane.

5. The agent according to claim 4, wherein the peptide comprises the residues rr N-terminal of the core sequence, and/or krk C-terminal of the core sequence.

6. The agent according to claim 1, wherein the peptide comprises or consists of the sequence:
rr-x3-k-x5-ktkkrk wherein (i) x3 is D-Phe and x5 is selected from D-Ala, D-Leu and Gly; or
(ii) x3 is D-Ala and x5 is selected from D-Val, D-Ala, D-Leu and Gly.

7. The agent according to claim 1, wherein the core sequence of Formula I is selected from the group consisting of akvk, fkak and akak.

8. The agent according to claim 2, wherein the core sequence of Formula II is selected from the group consisting of akvktk, fkaktk and akaktk.

9. The agent according to claim 1, wherein the peptide comprises or consists of the sequence:
rrakvktkkrk
or
rrfkaktkkrk.

10. The agent according to claim 1, having the formula
$R^1$—Z—$R^2$ wherein:

$R^1$ is H, $C_{1-4}$ alkyl, acetyl, formyl, benzoyl or trifluoroacetyl;
$R^2$ is OH or $NH_2$;
and Z represents a peptide sequence as described in claim 1.

11. The agent according to claim 10, which is:
H-rrakvktkkrk-$NH_2$
or
H-rrfkaktkkrk-$NH_2$.

12. A pharmaceutical composition comprising the agent according to claim 1 and a pharmaceutically acceptable carrier.

13. The pharmaceutical composition of claim 12 further comprising a substance to be delivered across an epithelial surface.

14. The pharmaceutical composition according to claim 13, wherein the substance is a diagnostic or therapeutic agent.

15. A kit comprising:

(i) a first composition comprising an agent according to claim 1; and (ii) a second composition comprising a substance to be delivered across an epithelial surface.

16. A kit according to claim 15, wherein the substance to be delivered is a diagnostic or therapeutic agent.

17. A method of increasing permeability of an epithelial surface comprising the step of administering the agent according to claim 1 to an epithelial surface.

18. A method of delivering a substance across an epithelial surface comprising the step of administering (a) the agent according to claim 1 and (b) a substance to be delivered across an epithelial surface to an epithelial surface.

19. The method according to claim 18, wherein the substance is a diagnostic or therapeutic agent.

\*    \*    \*    \*    \*